US008478534B2

(12) United States Patent
Zhu et al.

(10) Patent No.: US 8,478,534 B2
(45) Date of Patent: Jul. 2, 2013

(54) METHOD FOR DETECTING DISCRIMINATORY DATA PATTERNS IN MULTIPLE SETS OF DATA AND DIAGNOSING DISEASE

(75) Inventors: Wei Zhu, Stony Brook, NY (US); Xuena Wang, Stony Brook, NY (US); John S. Kovach, Setauket, NY (US)

(73) Assignee: The Research Foundation For The State University of New York, Albany, NY (US)

( * ) Notice: Subject to any disclaimer, the term of this patent is extended or adjusted under 35 U.S.C. 154(b) by 1259 days.

(21) Appl. No.: 10/868,387

(22) Filed: Jun. 14, 2004

(65) Prior Publication Data
US 2005/0022168 A1 Jan. 27, 2005

Related U.S. Application Data

(60) Provisional application No. 60/477,529, filed on Jun. 11, 2003, provisional application No. 60/553,433, filed on Mar. 15, 2004.

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS 6,389,436 B1 * 5/2002 Chakrabarti et al. ......... 715/229
6,591,235 B1 * 7/2003 Chen et al. .................... 704/236

2002/0192655 A1 12/2002 Ginns et al.
2003/0004402 A1 1/2003 Hitt et al.
2004/0225202 A1 11/2004 Skinner

OTHER PUBLICATIONS

Kantarci et al. Journal of Neuroimmunology, vol. 123, 2002, pp. 144-159.*
Quackenbush J. New England Journal of Medicine, vol. 354, 2006, pp. 2463-2472.*
Sorace et al. BMC Bioinformatics, vol. 4, pp. 1-13, Jun. 9, 2003.*
Flandin et al. LNCS, vol. 2488, pp. 467-474, 2002.*
"Use of Proteomic Patterns in Serum to Identify Ovarian Canncer" by Petricoin et al., The Lancet, vol. 359 pp. 572-577, Feb. 18, 2002.
"Correspondence" The Lancet, vol. 380 pp. 169-171, Jul. 13, 2002.
Rocus et al. Effectiveness of Extreme Discordant Sib Pairs to Detect Oligogenic Disease Loci, Genetic Epidemiology. Oct. 1996, vol. 14, pp. 879-884, entire documents.
Fullerton et al. Linkeage Analysis of Extremely Discordant and Concordant Sibling Pairs Identifies Quantitative-Trait Loci that Influence Variation in the Human Personality Trait Neuroticism. Am. J. Hum. Genet. Apr. 2003, vol. 72, pp. 879-890.

* cited by examiner

*Primary Examiner* — Jason Sims
(74) *Attorney, Agent, or Firm* — The Farrell Law Firm, P.C.

(57) ABSTRACT

A comprehensive analysis procedure for analyzing and comparing multiple sets of data to detect hidden discriminatory data patterns. The inventive procedure identifies a best subset of markers for optimal discrimination between two or more sets of data. A point-wise test on two or more sets of data is performed to calculate test statistic values and to generate a statgram, a two- or higher- dimensional map of the test statistic values along the range of data. A threshold is then determined for isolating critical regions of the statgram at each significance level to provide candidate markers. A subset of markers from the candidate markers is then selected to discriminate among the sets of data. The two or more sets of data are classified using the subset of markers.

26 Claims, 7 Drawing Sheets

Figs. 2A-H

Fig. 4. Statgram

Fig. 6A
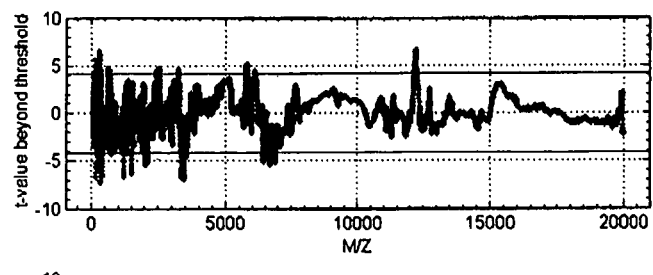
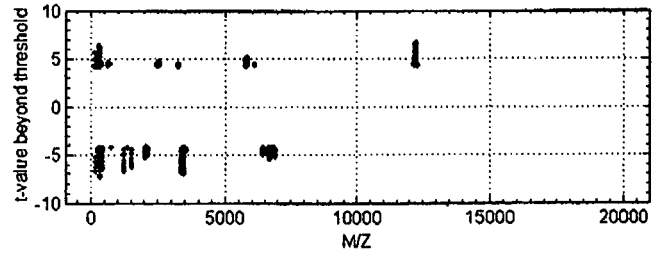
Fig. 6B

METHOD FOR DETECTING DISCRIMINATORY DATA PATTERNS IN MULTIPLE SETS OF DATA AND DIAGNOSING DISEASE

RELATED PATENT APPLICATIONS

The present application claims priority from U.S. Provisional Patent Application No. 60/477,529 filed on Jun. 11, 2003 and from U.S. Provisional Patent Application No. 60/553,433 filed on Mar. 15, 2004, each of which is entitled A METHOD AND SYSTEM FOR DETECTING DISCRIMINATORY DATA PATTERNS BETWEEN MULTIPLE SETS OF DATA and each of which is incorporated herein by reference in its entirety.

FIELD OF THE INVENTION

The present invention relates to methods and systems for analyzing data, particularly for detecting patterns that distinguish multiple sets of data.

BACKGROUND OF THE INVENTION

In many systems or phenomena, naturally occuring or otherwise, distinctive patterns of data are often buried within the highly complex data sets that are created to characterize such systems or phenomena. Such patterns have been observed, for example, in the study of a wide variety of systems and phenomena such as diseases, environmental conditions, and financial conditions, to name a few.

The distinctive patterns of data that may characterize certain conditions are often not obvious or apparent using existing classification methods and systems. The current classification systems and methods typically find or uncover a single known differentiating feature between sets of data or analyze only a subset of the data. A hidden pattern found in one dataset is generally not applicable to another dataset. That is, these systems generally require "retraining" on each new set of data and cannot completely characterize the dataset.

For example, current classification systems cannot effectively screen for early stage ovarian cancer. In its early stages, ovarian cancer is an insidious disease, exhibiting essentially no symptoms. Ovarian tumors may grow to a size of about 10-12 cm before impinging on adjacent organs, resulting in symptoms, such as increased urinary frequency and rectal pressure. More than 80% of ovarian cancer patients currently are diagnosed at a late clinical stage as a result of the absence of early stage symptoms and the associated 5-year survival rate is only 35%. If ovarian cancers are diagnosed at an early stage, however, the 5-year survival rate is more than 90% because, in most cases, the cancer can then be eradicated completely by surgery.

An estimated 25,000 women are diagnosed with ovarian cancer annually in the United States and approximately 14,500 women die from the disease each year. An effective screening program for early stage ovarian cancer has been elusive, however, due to factors which include the lack of a highly specific screening test. With the rapid development of proteomics, new screening strategies utilizing modern proteomic technology and bioinformatics are emerging, but none have shown sufficient specificity to be an effective diagnostic tool.

The PROTEIN CHIP array surface-enhanced laser desorption-ionization (SELDI) mass spectrometry (MS) system, available from Ciphergen Biosystems of Fremont, CA, USA, is increasingly recognized as the leading technology for fast and reliable protein profiling based on tissue or body fluid samples. The underlying principle of SELDI is surface-enhanced affinity capture through the use of specific probe surfaces or protein chips. Once captured on the SELDI protein chip array, proteins are detected through the ionization-desorption, time-of-flight mass spectrometry process. The PROTEIN CHIP SELDI-MS has been useful in identifying known markers of prostate cancer and in discovering potential markers which are over- or under- expressed in prostate cancer cells and body fluids.

By comparing serum proteomic spectra of early stage ovarian cancer patients with a comparable group of unaffected women using a bionformatics algorithm, a recent study has identified a set of proteomic markers and has been able to classify subjects with a sensitivity of 100% and a specificity of 95%. See Petricoin et al. "Use of Proteomic Patterns in Serum to Identify Ovarian Cancer," The Lancet, vol. 369, pp. 572-577 (Feb. 16, 2002), incorporated herein by reference in its entirety and hereinafter referred to as the "Lancet Paper;" and U.S. Published patent application Ser. No. 2003/0004402 A1, entitled "Process for discriminating between biological states based on hidden patterns from biological data," also incorporated herein by reference in its entirety.

Shortly after the publication of the Lancet Paper, using the same set of subjects and an improved protein surface, Petricoin et al. achieved better results with a sensitivity of 100% and a specificity of 97%. See "Correspondence," The Lancet, vol. 360, pp. 169-171 (Jul. 13, 2002), incorporated herein by reference in its entirety and hereinafter referred to as the "Correspondence." The corresponding proteomic mass spectrum data set (referred to as "ovarian data set 4-3-02") is publicly available at the NTH/FDA Clinical Proteomic Program Databank website.

While applauding their accomplishment, many remained skeptical about the screening value of the method described by Petrocoin et al. in the Correspondence. In fact, Petrocoin et al. stated that the prevalence of ovarian cancer in postmenopausal women is 1 in 2,500, which means that a screening assay with 97% specificity would result in 75 false positives for every true positive identification.

There are several statistics based, analytical tools that have been developed to analyze mass spectra of protein marker expression for various disorders. The genetic algorithm first described by John Holland in the mid-1970s manipulated complex data sets as individual elements through a computer-driven analog of a natural selection process. In 1982, Kohonen proposed a cluster analysis method by using a self-organizing map. Correlogic Systems, Inc. of Bethesda, Maryland has combined the ideas of Holland's genetic algorithm and Kohonen's self-organizing map to implement a pattern discovery algorithm in a software named PROTEOME QUEST (genetic algorithm and self-organizing map software for implementing pattern discovery), Beta version 1.0. Petricoin et al. utilized the PROTEOME QUEST (genetic algorithm and self-organizing map software for in pattern discovery) software to analyze the proteomic spectra generated by SELDI-TOF, to identify ovarian cancer. Petricoin et al. adopted a random window approach to sequentially select markers and to examine their contribution towards the classification rate.

A drawback to Petricoin et al.'s approach is that only portions of the proteomic spectra are used for the analysis, in which case the contribution of each marker may vary with the window size and significant protein markers may be excluded from the analysis. Conversely, many of the biomarkers predicted by such known methods will not be statistically significant, so that in many cases, efforts to determine the underlying molecular identity and subsequent cell and molecular biology will be fruitless.

For the large-scale screening for the presence of early cancer, specificity and sensitivity must approach 100% to assure no disease is missed and to prevent pursuit of unnecessary additional diagnostic procedures. Similarly, biomarker identification and molecular characterization require a high degree of reproducibility and fidelity for each individual proteomic marker.

Another challenge when analyzing proteomic data (or genomic data, in general) is to draw robust conclusions from high-dimensional data based on relatively few subjects. The question is how robust this conclusion is. In addition to providing 100% accuracy and specificity when analyzing a particular testing set, a robust analysis method should be able to determine discriminating markers that can be trusted to accurately diagnose any random subject from relevant population at large. In other words, 100% accuracy and specificity should apply to the full population.

In light of the known approaches and their limitations, it is clear that improved analysis methods and systems are required. Moreover, it is desirable to have a comprehensive method and system that considers each data point of the dataset to discover hidden patterns or markers, thereby enabling the method and system to detect subtle differences in multiple datasets without retraining on each dataset. Such a system and method trained, for example, to detect a toxin from an environmental dataset can be used on another environmental dataset to detect that toxin without retraining on the other environmental dataset.

SUMMARY OF THE INVENTION

The present invention provides a method and system for analyzing multiple sets of data, more particularly a comprehensive method and system for detecting subtle hidden differences among multiple sets of data. The comprehensive method and system obtains best discrimination between multiple sets of data that can be expressed with one or more common coordinates. The inventive method and system performs a point by point assessment of the data, thereby enabling the present invention to detect subtle differences in the data that cannot be detected by current analytical methods.

An exemplary embodiment of a method of the present invention performs a point-wise test on two or more sets of data to calculate test statistic values and to generate a statgram, a two-, or higher, dimensional map of the test statistic values along the range of data. A threshold is then determined for isolating critical regions of the statgram at each significance level to provide candidate elements. A subset of elements from the candidate elements is then selected to discriminate among the sets of data. The two or more sets of data are classified using the subset of elements.

An exemplary embodiment of a system of the present invention comprises a statgram module, a threshold module, a marker selection module and a classifier. The statgram module performs a point-wise test on the sets of data to calculate test statistic values and generate a statgram. The threshold module determines a threshold to determine critical regions of the statgram at each significance level to provide candidate elements and the marker selection module selects a subset of elements from the candidate elements to discriminate the sets of data. The classifier classifies the sets of data using the subset of elements.

The comprehensive statistical method and system of the present invention can analyze biological datasets or non-biological datasets to detect the presence of unique data, elements or markers, or quantitative differences in the same data elements or markers.

The present invention is applicable to a wide range of fields including, for example, biology, medicine, chemistry, and economics.

In an exemplary embodiment of the present invention, environmental samples such as air samples, soil samples and water samples are compared and analyzed to detect the presence of a particular substance or radiation in the environment, thereby providing a bio-hazard detector, for example.

In another exemplary application of the present invention, the comprehensive method and system analyzes and compares tissues and body fluids (such as serum) of diseased and control subjects so as to draw conclusions regarding, for example, the existence, progression or regression of a diseased state. An exemplary embodiment of the present invention examines the complete proteomic spectrum of biological samples and selects all of the significantly different biomarkers using random field theory. A best-subset discriminant analysis is then used to choose the most significant biomarkers. An exemplary embodiment of the present invention is described below in connection with the early diagnosis of ovarian cancer. This embodiment has been used to re-analyze two public ovarian cancer data sets with 100% specificity and 100% sensitivity.

It is an object of the present invention to overcome the shortcomings of known methods described supra.

Another object of the present invention is to provide a comprehensive analytical method and system for detecting discriminatory data patterns between sets of data where each data element can be described by one or more coordinates.

A still other object of the present invention is to provide a comprehensive analytical method and system as aforesaid, which performs a point by point assessment of the data to detect subtle differences in the datasets without retraining on each dataset.

A further object of the present invention is to provide a computer readable medium comprising a code for detecting discriminatory data patterns between sets of data, each data element being described uniquely by one or more coordinates. The code comprising instructions for performing a point-wise test on the sets of data to calculate test statistic values and generate a statgram, determining a threshold to determine critical regions of the statgram at each significance level to provide candidate elements, selecting a subset of k elements from the candidate elements to discriminate between the sets of data, and classifying the sets of data using the subset of k elements.

A still further object of the present invention is to provide a comprehensive analytical method and system for analyzing and comparing sample data (e.g., tissue and body fluids, such as serum) of affected (i.e., subjects having a disease or disorder or a predisposition for a disease or disorder) and control (unaffected) subjects e.g., via analysis of protein mass spectra. The inventive method identifies a best subset of "k" elements or markers, where "k" is any positive integer, found in the sample data (e.g., serum) to allow for optimal discrimination between two or more groups.

The markers are identified as potential candidates for further biological examination, so as to identify markers involved in the disorder or disease. As discussed below, the inventive methodology achieved perfect discrimination (100% sensitivity, 100% specificity) between patients with early stage ovarian cancer and normal controls (including benign cases). Ovarian cancer diagnosis is exemplary of the inventive technique, which is not only invaluable in screening for ovarian cancer, but can be used for early diagnosis, treatment development and evaluation of patients where any disease or condition of interest is involved.

In accordance with an embodiment of the present invention, the comprehensive analysis method and system examines and quantifies the role of each protein marker along the mass spectrum. All markers with significantly different expression levels between the affected and unaffected subsets, at a given experimentwise error rate, are selected for the ensuing best-subset discriminant analysis to determine the optimal set of markers for diagnosis of the disorder or disease, such as cancer. The inventive method is highly effective for, e.g., ovarian cancer detection, as it achieved perfect discrimination between diseased and normal subjects (including benign cases).

It is a further object of the present invention to provide a method and system for the longitudinal analysis of a time series of mass spectra, such as serum protein mass spectra.

The foregoing has outlined rather broadly the features and technical advantages of the present invention in order that the detailed description of the invention that follows may be better understood. Additional features and advantages of the present invention will be described hereinafter which form the subject of the claims of the invention. It should be appreciated by those skilled in the art that the specific concepts and embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 6A is a graph illustrating the statgram of FIG. 4 with positive and negative thresholds drawn at the critical value of 4.22 and FIG. 6B shows the statgram at values beyond the thresholds, thereby showing the markers remaining after the thresholding procedure.

DETAILED DESCRIPTION

Figure 1:
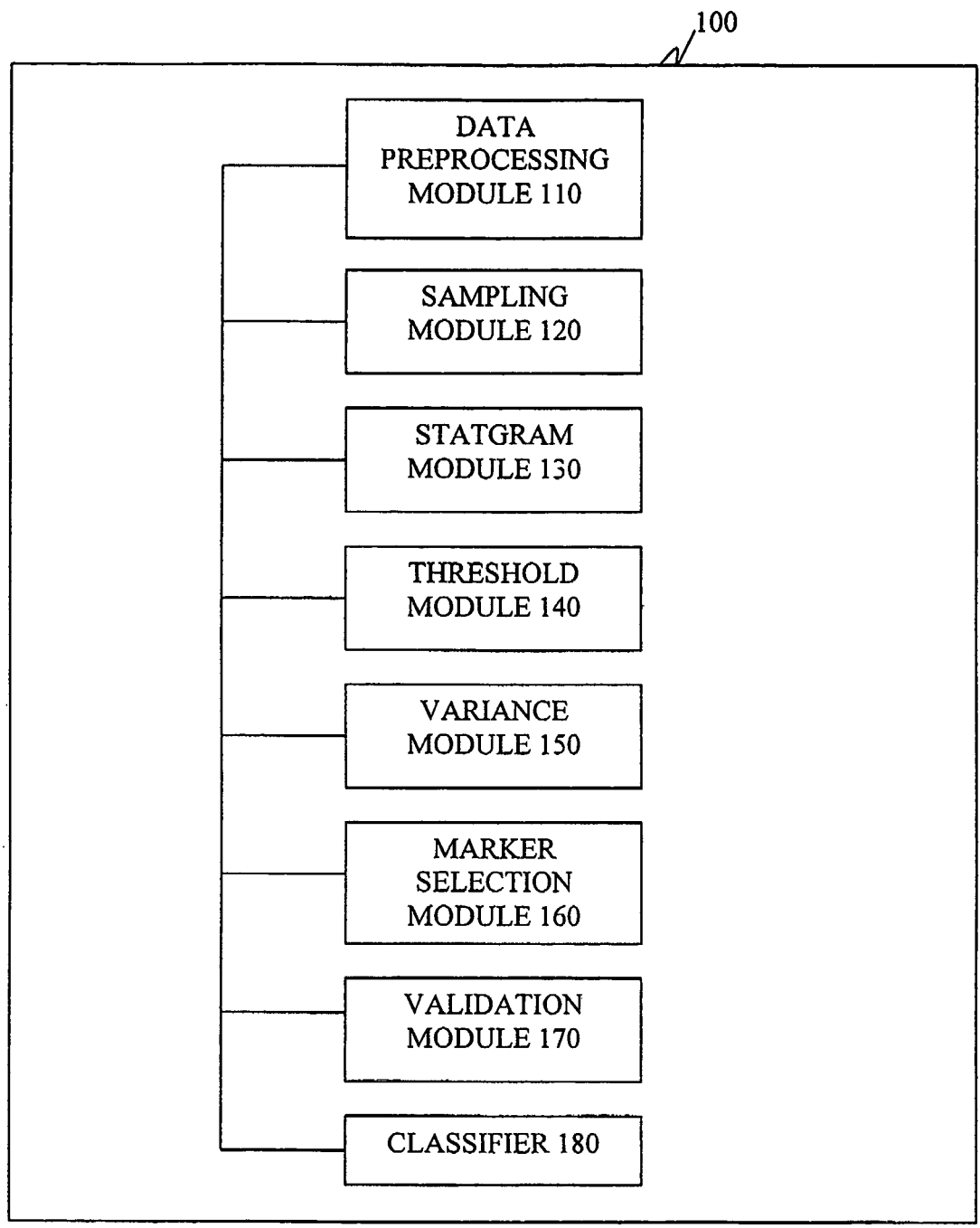
FIG. 1 is a functional diagram of a computer 100 in accordance with an embodiment of the present invention.

The comprehensive statistical method of the present invention can be applied to analyze any type of raw data, including clinical or environmental data where the sample may be, e.g., water, air, soil, serum, blood, saliva, plasma, nipple aspirate, synovial fluid, cerebrospinal fluid, sweat, urine, fecal matter, tears, bronchial lavage, swabbings, needle aspirant, semen, vaginal fluid, pre-ejaculate, etc., to carry out, e.g., screening for contaminants, pathologic diagnosis, toxicity status, efficacy of a drug, screening or prognosis of a disease. In fact, the present invention can be used to analyze any data that can be expressed with common coordinates. That is, the multiple sets of data can be mapped into the same coordinate system, thereby enabling comparison between multiple sets of data. Moreover, the present invention can analyze data from mass spectroscopy, liquid chromatography, two-dimensional gel chromatography, gas chromatography, etc.

In accordance with an embodiment of the present invention, the comprehensive statistical method and system can be used to analyze spectrum data of tissues or body fluids (referred to collectively as the "biological sample") for pattern detection and discrimination purposes (i.e., diseased and non-diseased subjects, or change in state of the disease). The following is a description of an exemplary embodiment of the present invention adapted to protein analysis of serum samples for the purpose of detecting ovarian cancer. Although the present invention is described herein with the ovarian cancer example, it is appreciated that the present invention can be applied to any multiple sets of data (including biological or non-biological data) that can be expressed with common coordinates to detect subtle hidden patterns and/or discriminate between multiple sets of data.

An embodiment of the present invention has been applied to the same set of ovarian cancer patients and normal subjects (including benign cases) analyzed by Petricoin et al. and described in the Lancet Paper and at the NIH clinical proteomics program website (the "Ovarian Dataset 4-3-02"). Although this exemplary application involves classifying or categorizing the data into two states or categories (i.e., normal and cancerous), it is appreciated that the present invention can classify or categorize the data into multiple states, e.g., normal, early stage cancerous and late stage cancerous. This can be done using the analysis of variance (ANOVA) F-test or the analysis of covariance (ANOCOVA) F-test for marker selection, described in greater detail below.

The disease status in the Ovarian Dataset 4-3-02 is given in Table I.

TABLE I

|  | Number of Subjects |
|---|---|
| Unaffected Women | |
| No evidence of ovarian cysts | 61 |
| Benign ovarian cysts <2.5 cm | 30 |
| Benign ovarian cysts >2.5 cm | 8 |
| Benign gynecological disease | 10 |
| No gynecological disease | 7 |
| Subtotal | 116 |
| Women with Ovarian Cancer | |
| Stage I | 24 |
| Stages II, III, IV | 76 |
| Subtotal | 100 |
| Grand Total | 216 |

The median ages of the 116 control subjects and the 100 ovarian cancer patients were 49 (range 21-75) and 58 (range 29-82), respectively. Based on the age distribution, premenopausal and postmenopausal women were equally represented in both groups (i.e., training data set and testing data set).

The serum protein mass spectrum generated for each subject was depicted by 15,200 mass over charge ratios (m/z values) on the x-axis and the corresponding intensity on the y-axis.

Figure 2:
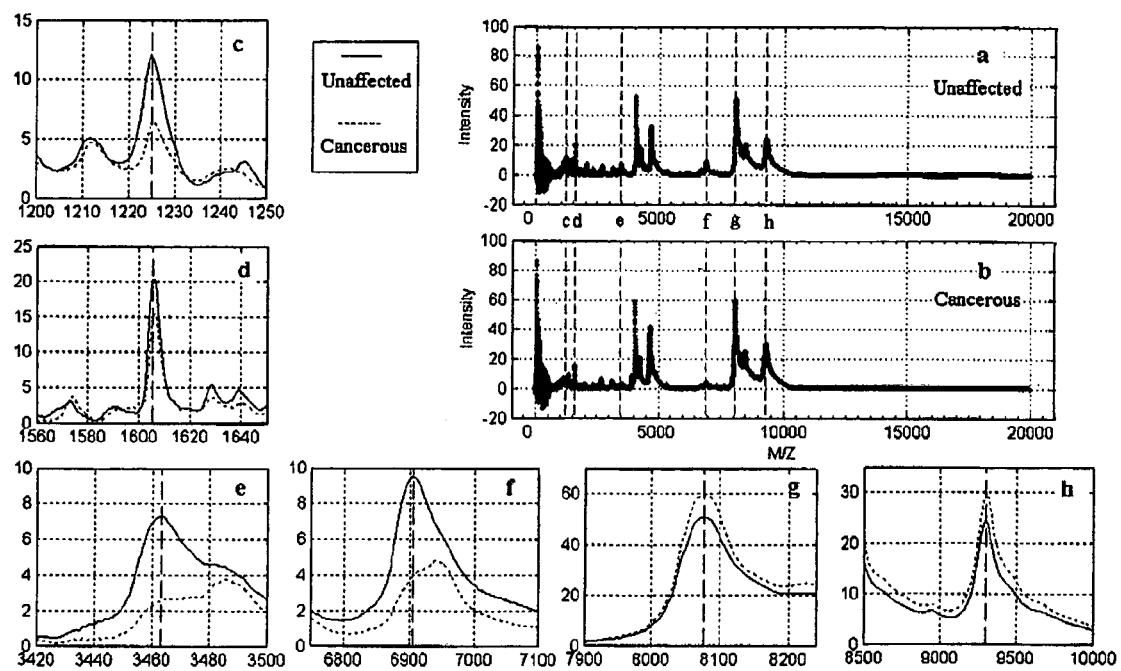
FIGS. 2A and 2B are average serum protein mass spectra of unaffected women and women with ovarian cancer, respectively.
FIGS. 2C-2H are magnified plots of various protein markers shown in FIGS. 2A and 2B.

FIGS. 2A and 2B depict the average spectrum intensity of 116 unaffected women and 100 women with ovarian cancer, respectively. As can be seen, there are significant differences in expression levels of certain protein markers, as shown in greater detail in FIGS. 2C-2H and indicated by dashed vertical lines in FIGS. 2A and 2B. A robust method, however, such as that of the present invention, can determine whether such potential differences in protein expression level are statistically significant (systematic and persistent in the population), as opposed to being due to random factors, such as outliers, sampling fluctuations, or the like.

Using the above-described ovarian cancer data, an exemplary embodiment of the present invention as applied to such data will now be described in greater detail.

Method

An exemplary embodiment of a method of the present invention includes a plurality of steps, each of which is described in greater detail below. Each step has a statistical basis and a probabilistic interpretation. The steps, in general, serve as filters, to reduce the size and dimensionality of the data processed by subsequent steps. For this reason, the computational efficiency of the early steps and their ability to reduce data dimensionality for the later steps are important.

At least two groups of data are initially provided, one being derived from a control group of unaffected subjects and the other being derived from a group of subjects affected by the condition of interest (e.g., ovarian cancer).

In an exemplary embodiment, the method of the present invention includes the following steps:

(1) Pre-processing the data on an individual group basis as necessary for the steps below and/or removing outlying data;
(2) Randomly selecting a training data set and a testing data set from each group of data;
(3) Performing a point wise two-sample t/z-test between the groups in the training data set, generating a map of the test statistic values (statgram);
(4) Selecting critical region(s) of the statgram based on a desired significance level;
(5) Selecting markers from the critical region(s);
(6) Checking the variance stability of the markers selected;
(7) Validating;
(8) Resampling (e.g., repeating steps 2-7); and
(9) Resolving any differences between the selected markers after steps 7 and 8, respectively.

Each step of this exemplary process is described below in greater detail.

Step 1: Pre-Processing the Data

The data is pre-processed as necessary for performing the other steps of the method, and/or to remove outliers. A purpose of such pre-processing is to reduce the noise content of the data and thus improve its signal-to-noise ratio. Such pre-processing also enables multiple-test correction via the random field theory, described in greater detail below.

In the exemplary embodiment, the data comprises mass spectral information indicative of molecules present in a biological sample, such as proteins in human blood. Pre-processing of the spectral data may include smoothing the data to obtain a Gaussian distribution. In particular, for a given group, an average spectrum is calculated and filtered to obtain a Gaussian distribution.

In an exemplary embodiment, the data pre-processing includes performing normalization to remove the overall variation of spectral strength between different subjects and smoothing via Gaussian filters, performed on each individual spectrum.

More particularly, the relative intensity for each mass spectrum is obtained by dividing the intensity at each m/z value (mass to charge ratio) by the average intensity of the entire spectrum. Such standardization ensures comparability across different spectra. Each relative spectrum is then smoothed by a Gaussian kernel with a full width half maximum (FWHM) value sufficiently small to preserve the original spectrum while being at least as large as the mass accuracy of the system used to generate the spectrum. For example, the mass accuracy of the Ciphergen system is 0.1%. Thus, a particle with a detected mass value of x could have the same true mass as particles in its neighborhood within a range of 0.2%x (i.e. x±0.1% x). It has been determined that the smallest FWHM that will achieve a mass accuracy of at least 0.1% for the entire spectrum is 11.

Figures 7A, 7B, 7C:
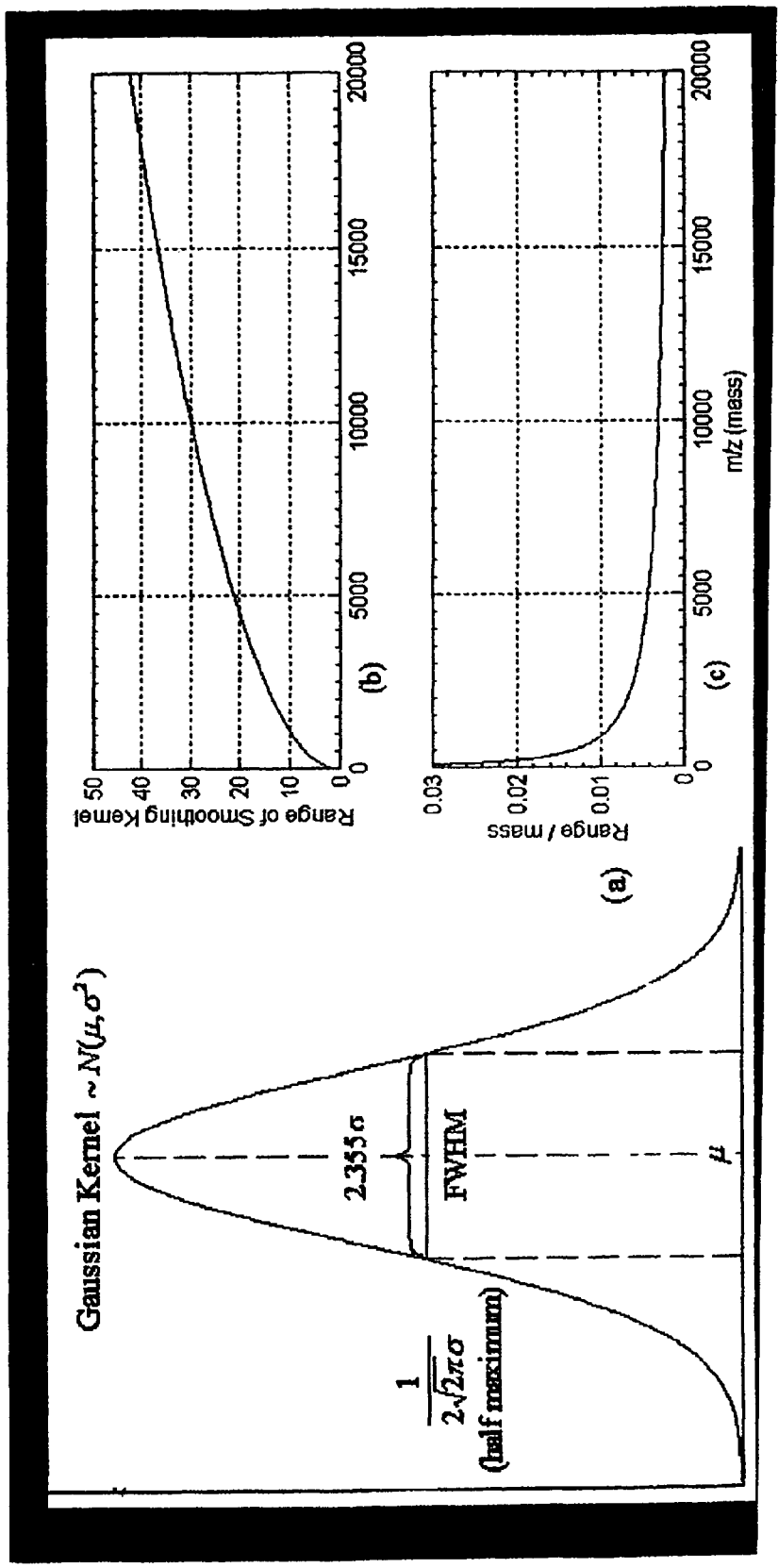
FIG. 7A is an illustration of a smoothing Guassian kernel for use in an exemplary embodiment of the present invention.
FIG. 7B shows the relationship between the range of the 11 adjacent points within the Gaussian smoothing kernel (y-axis) and the median of the range (x-axis) when FWHM=11, as in the exemplary embodiment.
FIG. 7C shows the relationship between the ratio of the range over its median (y-axis) and the median of the range (x-axis) when FWHM=11.

FIG. 7A is an illustration of a Guassian kernel as used in a data pre-processing step of an exemplary embodiment of the present invention. The smoothed intensity of the biomarker with m/z value µ is calculated as the weighted average, proportional to the Gaussian density, of the intensities of its neighboring biomarkers.

FIG. 7B shows the relationship between the range of the 11 adjacent points within the Gaussian smoothing kernel (y-axis) and the median of the range (x-axis) when FWHM=11, as in the exemplary embodiment.

FIG. 7C shows the relationship between the ratio of the range over its median (y-axis) and the median of the range (x-axis) when FWHM=11. As shown in FIG. 7C, for FWHM =11, the ratio of the range over its median (y-axis) is above 0.002 (0.2%) for most of the spectrum and approaches 0.002 only toward the highest m/z values of the spectrum.

Step 2: Creating a "Training Set" and a "Testing Set"

After standardization and smoothing, the subjects are divided into a training set and a testing set. The training set comprises a predetermined number of subjects selected at random from the group of subjects known to have the condition of interest and a predetermined number of subjects selected at random from the group of subjects known not to have the condition of interest. The testing set comprises the remaining subjects. For example, in an exemplary processing of the above-described Ovarian Dataset Apr. 3, 2002, of the 216 subjects, the training set consisted of a random sample of 50 subjects with ovarian cancer and a random sample of 50 unaffected subjects. The testing set consisted of the remaining 116 subjects, 50 of which were affected and 66 of which were unaffected.

Step 3: Creating a Statgram

Once the training and testing sets have been created, a statgram is generated based on the data of the subjects in the training set. In the exemplary embodiment in which the data is proteomic spectral information, the statgram is a two-dimensional map of test statistic values along the range of m/z values. In order to generate the statgram, an independent samples t/z test is performed at each m/z value to compare the spectral intensities between the two groups of subjects (i.e., affected and unaffected) in the training set. (The z-test is preferably used when both sample groups are large, whereas the t-test is preferably used when at least one sample group is small. For exemplary ovarian cancer application, the z-test is used.) The null hypothesis is that the intensities are equal between the groups at each m/z value and the alternative hypothesis is that they differ.

The test statistic value t(x) at each m/z value (x) is determined as follows:

$$t(x) = \frac{\overline{y_1}(x) - \overline{y_2}(x)}{\sqrt{s_1^2(x)/n_1 + s_2^2(x)/n_2}} \quad \text{(Eq. 1)}$$

where $\overline{y}_1(x)$, $\overline{y}_2(x)$, $s_1^2(x)$, and $s_2^2(x)$ are the means and standard deviations, respectively, of the training samples and $n_1$ and $n_2$ are the numbers of training samples in each of the two groups in the training set.

Figure 4:
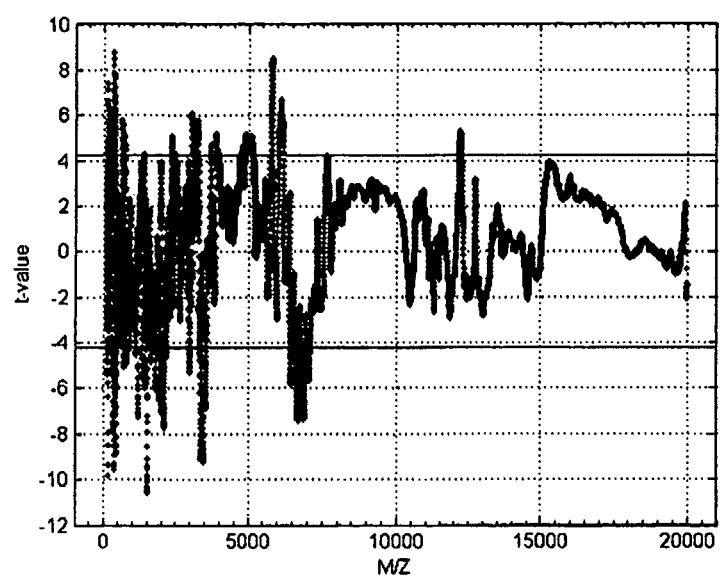
FIG. 4 is a graph illustrating an exemplary statgram in accordance with an exemplary embodiment of the present invention.

The test statistic values t(x) are plotted against the m/z values (x) to generate the statgram. FIG. 4 shows an exemplary statgram for an embodiment of the present invention adapted to the study of ovarian cancer. In the case where both samples are large (e.g., in the example above where $n_1=n_2=50$), the test statistic t(x) follows approximately the standard normal distribution under the null hypothesis.

At each m/z value (x), the larger the absolute value of the test statistic t(x), the stronger the evidence supporting the alternative hypothesis that the average spectral intensities are different between the two groups. As such, those m/z values tend to be indicative of possibly significant markers.

Step 4: Thresholding the Statgram—Multiple-Test Correction and Critical Region Selection Once the statgram has been generated, as described above, a thresholding procedure is carried out in which those regions of the statgram are selected in which the absolute value of the test statistic exceeds a critical value (or threshold) determined as a function of a desired significance level.

When only one test is performed (i.e., for one m/z value), one would reject the null hypothesis at a significance level of 0.05 if |t(x)| exceeds the critical value of 1.96 for the z-test. In other words, for an m/z value for which the absolute value of the test statistic (determined per eq. 1) is greater than 1.96, there is a 95% probability that the difference in spectral intensities between the affected and unaffected groups at that m/z values is a real difference (i.e., true for the populations) and not just a spurious difference that may be caused by the variability in random sampling or the like. However, since the total number of tests will be equal to the total number of data points in each spectrum, the confidence level would be much lower than 95% for the entire set of tests if each test were to be conducted at the significance level of 0.05. To determine a suitable significance level for each test, a multiple-test correction is performed so to have 95% confidence that differences identified are real.

There are several methods available for multiple-test correction such as the Bonferroni method, the Tukey method, and the random field theory (RFT) method. Methods such as the Tukey and Bonferroni methods tend to be more conservative than the RFT method. In an exemplary embodiment, RFT is employed for the multiple-test correction. A prerequisite for RFT multiple-test correction is that each spectrum be a one-dimensional Gaussian field. This can be achieved by presmoothing the spectral data with a Gaussian kernel, as described above. The Gaussian kernel is uniquely determined by its FWHM.

The relationship between the experimentwise error rate α and the critical value t for each z-test is given by the following expression:

$$\alpha \approx \int_t^\infty \frac{1}{\sqrt{2\pi}} e^{-u^2/2} du + \frac{K\sqrt{\ln 2}}{\pi(FWHM)} e^{-t^2/2} \quad \text{(Eq. 2)}$$

where K is the total number of tests.

The relationship between the experimentwise error rate α and the critical value t for each t-test with v degrees of freedom is given by the following expression:

$$\alpha \approx \int_t^\infty \frac{\Gamma\left(\frac{v+1}{2}\right)}{\Gamma\left(\frac{v}{2}\right)\sqrt{v\pi}} \left(1 + \frac{u^2}{v}\right)^{-\frac{v+1}{2}} du + \frac{K\sqrt{\ln 2}}{\pi(FWHM)} \left(1 + \frac{t^2}{v}\right)^{-\frac{v+1}{2}} \quad \text{(Eq. 3)}$$

Figure 5:
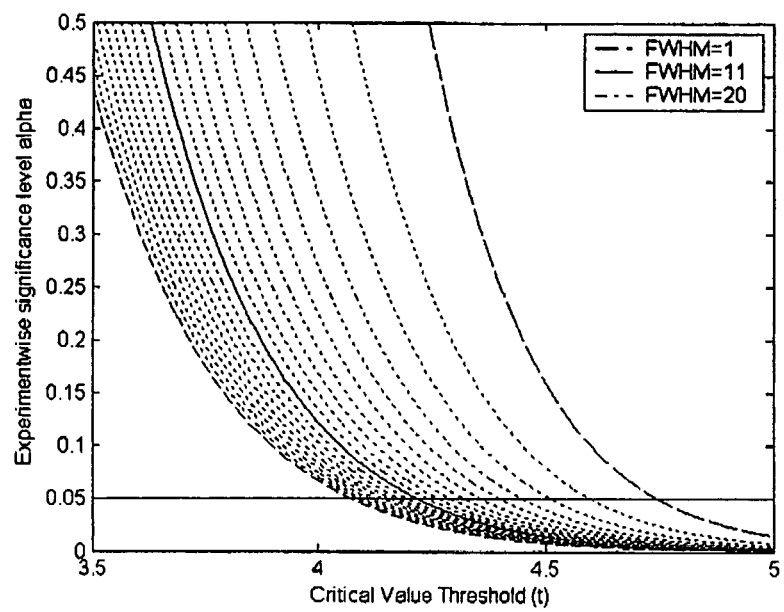
FIG. 5 is an exemplary graph illustrating the relationship between full width at half maximum (FWHM) experimentwise error rate and critical value threshold.

FIG. 5 shows the relationship between the experimentwise error rate α and the critical value t for different Gaussian smoothing kernels. As shown in FIG. 5, there is little variation in the critical value when the Gaussian kernel FWHM varies between 10 and 20 data points. As described above in connection with step 1, a Gaussian smoothing kernel with FWHM of 11 is used in the data preprocessing step in an exemplary embodiment of the present invention. Furthermore, in the exemplary embodiment, the spectrum for each subject tested has 15,154 m/z ratios (i.e., K=15,154). In order to achieve an error no higher than α=0.05 (2-sided), the critical value t in accordance with RFT multiple-test correction is determined to be 4.22.

The critical value generated by the RFT method is less conservative than the critical value that would be generated by the Tukey or Bonferroni methods. For example, to ensure an experimentwise error rate of 0.05 (2-sided), the Bonferroni method requires that each test be performed at the significance level of $0.05/15154=3.299459 \times 10^{-6}$ (2-sided). The corresponding critical value for a normal test is 4.65. That is, using Bonferroni multiple-test correction, the null hypothesis of equal intensity at a given m/z value (x) would be rejected if |t(x)|>4.65.

Using the critical value thus determined, the statgram derived above is then thresholded; i.e., those points on the statgram for which the test value exceeds 4.22 (or is less than −4.22) are selected. In other words, when thresholding at the critical value of 4.22, data points with |t(x)|>4.22 are considered significantly different between the two groups of subjects at the significance level of 0.05 and are adopted as candidates for a discriminant analysis phase.

Although a significance level of 0.05 has been used in this exemplary application, the significance level can be any value between 0 and 1.

FIGS. 6A and 6B illustrate the exemplary statgram before and after thresholding, respectively. By thus applying RFT multiple-test correction, the effective number of tests is reduced from 15,154 to about 563. In essence, the reduction is achieved by eliminating redundant tests for m/z values within the same smoothing kernel.

By thresholding at the critical value of 4.22, 563 tests remain significant. The corresponding 563 protein biomarkers are considered significantly different between the unaffected and affected populations and can be adopted as candidates for the discriminant analysis. These statistically significant biomarkers are valuable for deriving a diagnostic/discriminant rule for the disease and for further biological studies to ascertain and understand their roles in the disease's development and progress and in the development of a new phenotype (other pathophysiologic states). This information is valuable for developing and evaluating therapeutic drugs and other treatments.

Step 5: Marker Selection

A subset of k markers from the candidates determined in step 4 that best discriminate between the two sets of training samples are selected for any user-defined positive integer k. The procedure starts from k=1 where k increases by 1 after each iteration until the discriminating performance reaches a plateau.

Once a subset of markers is identified, test subjects can be classified in accordance with the marker values for those subjects. Non-parametric classification methods that can be used include the l-nearest neighbor classification method, and the uniform kernel method. The l-nearest neighbor classification method is equivalent to the uniform kernel method with a location dependent radius. Both methods tend to produce similar results. In an exemplary embodiment, l-nearest neighbor classification is used because of its robustness, flexibility, and intuitive explanations. Other non-paramteric and parametric methods may also be used, such as the normal kernel method as well as a neural network classification method.

In accordance with the l-nearest neighbor classification method, for each subject in the testing set, the l nearest neighbors in the training set are determined. The condition of the majority of the l nearest training set neighbors determines the predicted condition of the testing subject. The l-nearest neighbor classification procedure depends on the "distances" between subjects. The "locations" of the subjects depend on the set of markers that are selected. In an exemplary embodiment, Mahalanobis distance is used. Mahalanobis distance is the covariance-adjusted distance between the mean marker scores of the subjects having the condition of interest (e.g. ovarian cancer) and the unaffected subjects, as defined by the training set.

Mahalanobis distance is based on the pooled variance-covariance matrix V. The squared distance between two observation vectors x and y is given by:

$$d^2(x,y)=(x-y)'V^{-1}(x-y). \quad \text{(Eq. 4)}$$

Here each vector corresponds to a subject. Its elements are the expression levels (intensities) of the k discriminating markers for the given subject.

For l-nearest neighbor classification, the choice of l is usually relatively uncritical. One approach is to try several different values of l to determine which value gives the best crossvalidated estimate of the classification rate. Crossvalidation treats n−1 out of n observations as a training set. It determines the discrimination functions based on the n−1 observations and then applies them to classify the one remaining observation. This is done for each of the n training observations. The classification rate for each group, that is, "sensitivity" for the affected group and "specificity" for the control group, is the proportion of sample observations in that group that are classified correctly. The next step is to determine whether the selected biomarkers distinguish the affected subjects from the unaffected subjects in the testing set.

In the above-described exemplary application in which 563 candidate markers are identified by random field theory correction, best separation between the two groups using the i-nearest neighbor classifier with l=5 is achieved when k=18 (i.e., there is 100% sensitivity and 100% specificity). In the above example, l=5. The smallest l that achieved perfect discrimination was used for the discriminant analysis of the remaining 116 spectra in the testing data set.

Step 6: Check Variance Stability

Checking variance stability is an optional step which may precede or follow the best discriminating subset selection procedure (step 5). The rationale for this step is that the expression level of certain markers may be correlated with stages of a condition or other individual traits, and therefore may have large variability across all subjects in a training set (affected or unaffected). By examining the coefficient of variation, a standardized measure of variability that is unaffected by the magnitude of the mean, one could establish a statistical threshold via resampling methods to divide the significant markers into two subsets-those with less and those with more variability. If a discriminant rule that is more robust to the condition's stages and individual traits is desired, only the more stable markers should be selected to derive the best k-subset of biomarkers. On the other hand, a more stage-sensitive discriminant rule can be derived by correlating more variable markers in the training set of the "affected subjects" with condition stages/severity.

Step 7: Validation

In an exemplary embodiment, a validation step is performed in which the testing set is scored. In a first embodiment, a binary decision is made using the l-nearest neighbor classification procedure (e.g., l=5) to score the subjects in the testing set as having the condition of interest (e.g., ovarian cancer) or not. For each subject in the testing set, the l nearest neighbors in the training set are determined. The condition of the majority of the l nearest training set neighbors determines the predicted condition of the testing subject. This procedure is described above.

The l-nearest neighbor classification procedure yields a binary outcome without attaching a probability indicative of the relative proximity of the given subject to each group. In a further embodiment, this limitation is addressed by integrating a scoring system that allows a probabilistic interpretation. In accordance with this embodiment, a probability that each subject in the testing set has the condition of interest is determined. The markers used in the scoring system can be all markers found significant from the random field marker selection step, or a best marker set with optimal classification rates, both obtained from the training set.

Suppose K markers are selected from the training set, and furthermore, suppose the mean and standard deviation for each marker in the training group are $\bar{x}_{ij}$ and $s_{ij}$, respectively, where i=1, 2 (1 representing the group with cancer and 2 representing the unaffected group), and j=1, 2, ..., K is the marker index. First consider the idealized case in which each distinct marker is statistically independent of the others. Then for a given subject in the testing set, the subject's score for the cancer and control groups are given by the following expression:

$$z_i = \sum_{j=1}^{K} \left[ \frac{y_j - \overline{x_{ij}}}{s_{ij}} \right]^2 \quad \text{(Eq. 5)}$$

These scores represent the statistical distance for each subject to the center of the cancer and control groups, respectively, for a single marker. The subject is more likely to belong to the group with a low z score, and the larger the difference between the two z scores, the higher the probability that the classification is correct.

Assuming the K selected markers are independent, the difference of the scores is proportional to the log likelihood ratio of the probability $L_i$ that the subject belongs to group 1 or group 2 respectively. This is expressed as follows:

$$\ln(L_1/L_2) = \sum_j [\ln(s_{2j}) - \ln(s_{1j})] - 0.5(z_1 - z_2) \quad \text{(Eq. 6)}$$

where:

$$L_i \prod_j 1/[\sqrt{2\pi}\, s_{ij}] \exp[-(y_j - \overline{x_{ij}})^2 / 2s_{ij}^2],$$

The realistic case with statistical dependencies among the markers can be derived naturally from the independent case by a change of variables that incorporates the covariance among the markers. The scoring system should be modified in this case using the Mahalanobis distance, expressed as follows:

$$z_i = (y - \overline{x_i})^T S_i^{-1} (y - \overline{x_i}) \quad \text{(Eq. 7)}$$

where $S_i$ is the sample variance-covariance matrix of the K markers for the cancerous training group (i=1) and the control training group (i=2), respectively.

In this general case:

$$\ln(L_1/L_2) = 0.5(\ln|S_2| - \ln|S_1|) - 0.5(z_1 - z_2) \quad \text{(Eq. 8)}$$

where:

$$L_i = \Pi_j 1/[(2\pi)^{K/2} |S_i|^{1/2}] \exp[-0.5(y - \overline{x_i})^T S_i^{-1}(y - \overline{x_i})]$$

At a given significance level, this subject will be assigned to group 1 if the log likelihood ratio exceeds a certain probability threshold (i.e. the difference in the z-score below the equivalent threshold) which will be determined by the likelihood ratio test. Similarly, the subject will be assigned to group 2 if the log likelihood ratio is below a certain threshold (i.e. the difference in z-score above the equivalent threshold) which will also be determined by the likelihood ratio test. For subjects whose score difference is between the two thresholds, additional tests, especially those with an independent or less correlated set of markers, are performed to further determine their status.

Step 8: Resampling

The markers that are significant as selected by the RFT thresholding procedure, tend to be dependent on the choice of the training set. To eliminate this dependency, the subject pool can be resampled to obtain alternate training set and testing set pairs. Stable markers that reappear with high frequency in the resampling process will be selected to choose the ultimate robust set of discriminating markers. Performance of the best subset selection of discriminating markers will be examined by cross-validation and other resampling schemes.

As mentioned, 100% specificity and 100% sensitivity have been achieved with the present invention. To determine whether the resultant specificity and sensitivity may have been due to a fortuitous choice of test and training sets, the entire process may be repeated by randomly selecting another training set. Steps 2 through 7 can be repeated one or more times. Consistency can thus be checked and distributions (of specificity, sensitivity, etc.) obtained.

System

In an exemplary embodiment, the method of the present invention can be implemented with a software program running on a processor or computer 100 of FIG. 1. The processor 100 analyzes each point of data in a set and determines whether it is statistically different from a comparable point in another set of data to thus discover data patterns, elements or markers, which differ either in their presence or in amount. In accordance with an embodiment of the present invention, the data can be classified or categorized into two or more states or categories In accordance with an embodiment of the present invention, the program comprises one or more modules or routines performing steps of the comprehensive statistical method. These modules and the steps they perform will now be described in greater detail.

Figure 3:
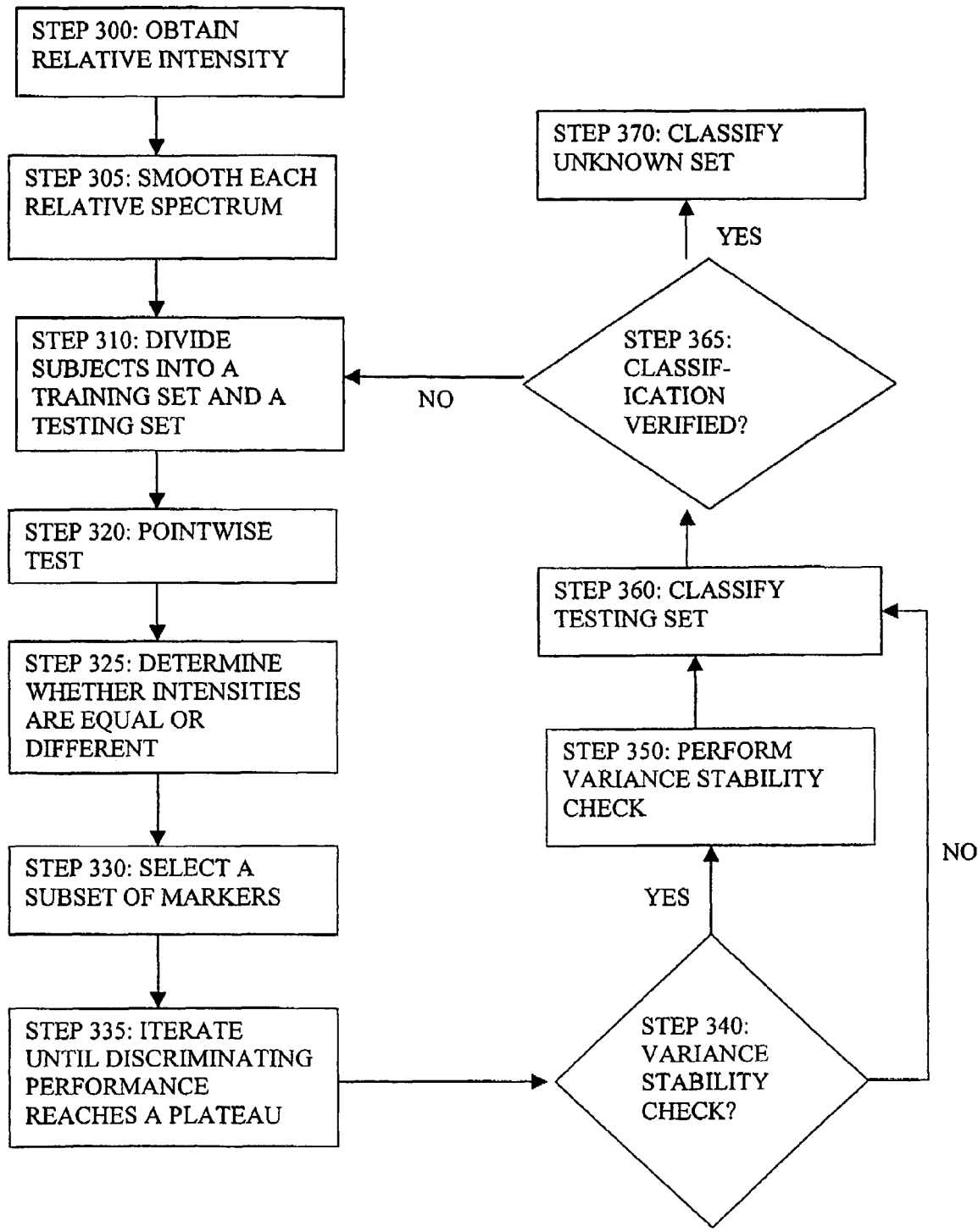
FIG. 3 is a flow chart detailing the process of analyzing serum protein mass spectra in accordance with an exemplary embodiment of the present invention.

FIG. 3 shows a flow chart detailing the process of analyzing serum protein mass spectra in accordance with an embodiment of the present invention.

The exemplary program comprises a data preprocessing module or routine 110 for data preprocessing, including standardization for relative spectrum and smoothing via Gaussian filters, performed on each individual spectrum. At step 300, the data preprocessing module 110 obtains the relative intensity for each mass spectrum by dividing the intensity at each m/z value with the average intensity of the entire spectrum. Such standardization provides comparability across different spectra.

At step 305, the data preprocessing module 110 may also smooth each relative spectrum by a Gaussian kernel having an appropriate full width at half maximum (FWHM), as described above.

As shown in FIG. 1, the exemplary program further comprises a sampling module or routine 120 for sampling for discriminant purposes. The sampling module 120 randomly selects a training data set from each group e.g., affected and unaffected, clean and contaminated, or state 1, 2, 3 . . . n, etc. The training data set could be the data for 10 out of 1,000 affected people, and 10 out of 10,000 unaffected people, for example. The remaining data is the testing data set. In the aforementioned example with 216 subjects, the sampling module 120 selects a random sample of 50 women with ovarian cancer and a random sample of 50 unaffected women for the training set. The remainder of 50 cancerous and 66 unaffected women comprises the testing set. The separation of the subjects into the training and testing sets is shown in the flowchart of FIG. 3 as step 310.

A statgram module or routine 130 is included for performing a pointwise test, such as a two-sample t/z-test, analysis of variance (ANOVA) F test, etc., between the groups in the training data set. As discussed above, a statgram is a two-dimensional map of the test statistic values along the spectrum. In the ovarian cancer application, the common coordinate shared between the data is the m/z value. Accordingly, the statgram module 130 performs an independent samples t/z-test at each m/z value to compare the intensity between the two training samples (cancerous and unaffected) at that m/z value. This is shown in the flowchart of FIG. 3 as step 320.

At step 325, the statgram module 130 determines whether the mean spectral intensities are equal (i.e., null hypothesis) or different (i.e., alternative hypothesis) between the groups at each m/z value. In accordance with an embodiment of the present invention, the statgram module 130 performs the t/z test at each m/z value (x) and determines the test statistic value t(x) in accordance with Eq. 1, as described above. The test statistic values are plotted against the m/z values generating a statgram, such as that shown in FIG. 4. Where both sample groups are relatively large (e.g., $n_1=n_2=50$, in the ovarian cancer data set), the test statistic t(x) follows approximately the standard normal distribution under the null hypothesis and thus the z-test is appropriate here.

A threshold module or routine 140 determines the threshold, based on multiple-test correction, that yields the critical regions of the statgram for a given desired significance level. At each m/z value, the larger the absolute value of the test statistic, the more likely it is that the statgram module 130 will determine in step 325 that the average intensities are different between the two groups (i.e., alternative hypothesis).

When only one test is performed, the threshold module 140 rejects the null hypothesis at the significance level of 0.05 (2-sided) if |t (x)| exceeds the critical value of 1.96. Although the significance level of 0.05 was used in this exemplary application, the significance level can be any value between 0 and 1.

In accordance with an embodiment of the present invention, the threshold module 140 performs a total of 15,154 tests to cover the entire m/z range for the exemplary application in step 325. To guard against falsely rejecting the null hypothesis, in accordance with an aspect of the present invention, the threshold module 140 performs a multiple-test correction. In accordance with an embodiment of the present invention, the threshold module 140 employs an RFT correction method, as described above.

As mentioned above, the data preprocessing module 110 pre-smoothes each spectrum with a Gaussian kernel so that each spectrum is a one-dimensional Gaussian field. The FWHM of the Gaussian kernel will likely range between 10 and 20. FIG. 5 shows that there is little variation in the critical value when the FWHM varies between 10 and 20.

As described above in connection with the exemplary ovarian cancer data, when the critical value of 4.22 is used as the threshold, the threshold module 140 determines that 563 tests out of the total of 15,154 tests are significant, as shown in FIGS. 6A and 6B. That is, the corresponding 563 protein markers are considered significantly different between the two populations (women with ovarian cancer and unaffected women) and are adopted as candidates by a marker selection module 160.

The exemplary program of the present invention may include a variance module or routine 150 for checking variance stability for selecting stable markers. If a user or operator requests a variance stability check in step 340, operation proceeds to step 350 in which the variance module 150 performs a variance stability check to determine if the selected markers are relatively stable. Performing a variance stability check may be desirable because the expression level of certain markers may be correlated with disease stages or other individual traits, and therefore may have large variability across all subjects in a training set (affected or unaffected). By examining the coefficient of variation (a standardized measure of variability that is unaffected by the magnitude of the mean), the variance module 150 can establish a threshold to divide the significant markers into two subsets: those with less and those with more variability.

In accordance with an embodiment of the present invention, the marker selection module 160 can be used in conjunction with the variance module 150 to derive a discriminant rule that is more robust to the various stages of the condition of interest and to individual traits. In step 330, the marker selection module 160 selects only stable markers to derive the best k-subset of markers. Alternatively, the marker selection module 160 can be used to find correlations between variable markers in the training set of affected subjects with condition stages/severity. A discriminant rule that is more sensitive to the various stages/severities of the condition can thus be derived.

Although not shown in FIG. 3, the variance module 150 can alternatively perform a variance stability check before the marker selection module 160 selects the k subset of candidate markers in step 330.

In the example described herein, the marker selection module 160 performs a best subset discriminant analysis to select the best subset of markers. In the exemplary ovarian cancer embodiment, 18 markers were selected from the 563 candidates remaining after thresholding of the statgram. The variance module 150 performs a variance stability check to determine whether the selected markers are relatively stable against the other markers. On the whole, the markers selected are relatively stable. The significance of the coefficient of variation for marker selection and data interpretation can be analyzed further when more subject-specific information is available.

The marker selection module or routine 160 selects a subset of k markers (k is a positive integer) from the list of markers remaining after processing by the threshold module 140 (or the variance module 150, if invoked or requested), that could best discriminate between the groups in the training set. The markers are selected via the best k-subset discriminant method. In accordance with an embodiment of the present invention, the marker selection module 160 selects the smallest k achieving the best possible classification performance. The marker selection module 160 starts from k=1 and k is incremented by 1 after each iteration until the discriminating performance reaches a plateau in step 335.

In the exemplary ovarian cancer case, the marker selection module 160 achieved the correct separation between the two groups when k=18. The 18 selected markers are shown in Table I below. The coefficient of variation (CV) in Table I is the ratio of the sample standard deviation and the sample mean. For each marker, the percentile (%) of its CV across the entire protein spectrum within each group is also given in Table II. Since markers within a neighborhood of 100 m/z values are likely to be variations of the same protein, the marker selection module 160 bins the selected markers into unique/independent groups for the ensuing biological validation. In the exemplary application, the marker selection module 160 effectively reduces the number of protein candidate markers from 18 to 10 independent groups to be used for further identification of their composition and validation of their role in ovarian cancer etiology.

TABLE II

Markers selected for the discriminant model

| M/Z | T-Value | Cancerous | | Normal | |
| --- | --- | --- | --- | --- | --- |
| | | CV | Percentile | CV | Percentile |
| 167.8031 | −5.7662 | 1.480295 | 82.52 | 0.625591 | 18.00 |
| 322.4204 | −5.9078 | 4.762101 | 98.52 | 1.40202 | 68.84 |
| 359.6322 | 7.731 | 0.292722 | 4.00 | 0.699381 | 23.93 |
| 385.5688 | 6.5828 | 0.239876 | 3.14 | 0.328497 | 3.32 |
| 434.6859 | −5.7399 | 2.299701 | 0.30 | 1.723423 | 79.78 |
| 444.469 | −8.8655 | 0.399504 | 6.85 | 0.440768 | 5.98 |
| 445.2563 | −8.5129 | 0.368993 | 5.93 | 0.419881 | 5.33 |
| 1222.185 | −4.7291 | 0.629668 | 28.22 | 0.575398 | 12.44 |
| 1528.343 | −5.8471 | 0.818051 | 42.04 | 0.661882 | 20.69 |
| 2026.812 | 3.8505 | 1.893308 | 89.69 | 1.281596 | 64.48 |
| 2522.814. | −4.1012 | 1.514503 | 83.35 | 1.266205 | 63.82 |
| 3345.8 | −9.1492 | 1.220903 | 71.54 | 0.98451 | 48.51 |
| 3449.15 | −6.592 | 1.208733 | 70.90 | 0.721731 | 25.31 |
| 3473.308 | −4.5641 | 0.867673 | 45.44 | 0.6403 | 19.31 |
| 3528.527 | 5.8663 | 0.772251 | 39.88 | 0.621775 | 17.70 |
| 6101.63 | 6.1853 | 0.645376 | 29.86 | 0.771314 | 28.80 |
| 6101.63 | 6.1853 | 0.645376 | 29.86 | 0.771314 | 28.80 |
| 6123.519 | −5.7609 | 0.538648 | 18.29 | 0.731008 | 26.04 |
| 6453.56 | −4.1838 | 3.809917 | 97.73 | 1.37106 | 68.03 |

At step 340, the processor determines if a variance stability check has been requested. If the user or operator does not request a variance stability check in step 340, operation proceeds to step 360 in which a validation module or routine 170 validates the selected k markers on a testing data set. In an exemplary embodiment, the l-nearest neighbor classification method is used to classify the testing data set and the sensitivity and specificity of the resulting classification are calculated. The validation module 170 performs discrimination and classification on the testing set using the normal kernel density estimates with unequal bandwidth.

In the exemplary ovarian cancer application, the validation module 170 correctly identified all 50 women with ovarian cancer of the testing set as positive and all 66 unaffected women of the testing set as negative. That is, the present invention achieved perfect discrimination with 100% sensitivity and 100% specificity of the test. The 95% confidence interval for sensitivity and specificity are (93%, 100%) and (95%, 100%), respectively.

In another application of the present invention, the processor 100 repeated steps 300-360 using another publicly available ovarian cancer data set with 162 cancerous and 91 unaffected women. ("Ovarian Dataset Aug. 7, 2002"; available from the above-cited NIH website). Again, the processor 100 obtained perfect sensitivity and specificity using the above procedures.

Furthermore, the 18 markers identified in the Ovarian Dataset Apr. 3, 2002 by the inventive system and method correctly classified (with 100% sensitivity and 100% specificity) all of the subjects of the Ovarian Dataset Aug. 7, 2002 via cross-validation. That is, the inventive system and method correctly classified 212 cancerous (162 from Dataset Aug. 7, 2002 and 50 from the testing set of Dataset Apr. 3, 2002) and 157 unaffected women (91 from Dataset Aug. 7, 2002 and 66 from the testing Dataset Apr. 3, 2002). The 95% confidence interval for sensitivity and specificity were (98%, 100%) and (98%, 100%); respectively The processor 100 can resample to check for consistency and to obtain distributions of specificity, sensitivity and the like, by repeating the process from the sampling module 120 to the validation module 170. In accordance with an embodiment of the present invention, the processor 100 repeats steps 310-360 in step 365 until the classification is verified. In analyzing the ovarian datasets described above, the sampling module 120 randomly selected another training set of 50 cancerous and 50 unaffected women in step 310. The processor 100 repeated or iterated steps 310-360 50 times and obtained 50 pairs of perfect discrimination.

After verifying the above results in step 365, a classifier module 180 of the processor 100 can be used in step 370 to screen unknown samples of serum for the presence of the pattern diagnostic of ovarian cancer.

In addition to Ovarian Datasets Apr. 3, 2002 and Aug. 7, 2002, the present invention has also been applied to another public data set of mass spectra of serum from ovarian cancer patients and control subjects (e.g., referred to as the "High Resolution Dataset", also available from the above-cited website). The High Resolution Dataset consists of spectra from 95 cancerous and 117 normal subjects, with the spectra obtained with a higher resolution mass spectrometer (QSTAR). Despite differences in the mass spectrometry platforms (low resolution SELDI-TOF versus high-resolution QSTAR) and differences in chip sample preparation (manual versus robotic), application of the present invention resulted in 100% specificity and 100% sensitivity in distinguishing sera from patients with ovarian cancer from those without cancer.

The method and system of the present invention select the best marker set from among markers that are differentially expressed among the groups of subjects being studied (e.g., cancerous and normal). Markers that are not statistically significant are removed from further analysis. Therefore, the markers selected are not only optimal for the given dataset but also tend to be robust and have excellent performance for independent datasets. For example, the best subset of 18 markers (Table II) selected from the Ovarian Dataset Apr. 3, 2002 can not only 100% classify the testing set for the Ovarian Dataset Apr. 3, 2002 data but also 100% classify the entire Ovarian Dataset Aug. 7, 2002, which consists of an entirely different set of subjects. These 18 markers are not only differentially expressed for the Apr. 3, 2002 data but also for the Aug. 7, 2002 data. The present invention thus provides a powerful systematic and robust methodology for the detection of subtle variations in serum protein patterns revealed by mass spectrometry.

A key difference between the present invention and other approaches such as that taken by the PROTEOME QUEST (genetic aigorithm and self-organizing map software for implementing pattern discovery) system, is that present invention selects markers that are statistically significant for the given study. That is, only markers exceeding certain statistical thresholds (determined, for example, by RFT) are chosen as candidate markers for the subsequent profiling. Consequently, the final protein profiles chosen by the present invention are by design, not only optimal for the given data sample, but also robust for the classification of subjects from other independent data samples from the same study population.

Table III shows that only a small fraction of markers exceeds the statistical threshold for each of the three ovarian cancer studies. The reduction in the data size as the method of the present invention progresses can be illustrated with its performance on these datasets. Thresholding results in reduction by a factor of 30. Clustering of the markers using the K-mean method (with the distance being 1- the Spearman correlation or the Pearson correlation), where applied, gives a further reduction by a factor of 2. Because the final step of selecting the marker subset tends to be computationally expensive, the desirability of data reduction before this step occurs is clear.

TABLE III

Successive stages of data analysis on the three public data sets.

| Data | Raw Data | Thresholded | Clustered | Selected |
|---|---|---|---|---|
| Apr. 3, 2002 | 15,154 | 563 | N/A | 18 |
| Aug. 7, 2002 | 15,154 | 867 | N/A | 6 |
| High-Resolution | 373,401 | 36,972 | 847 | 107 |

Although the PROTEOME QUEST (genetic algorithm and self-organizing map software for implementing pattern discovery) algorithm did obtain perfect classification on both the 8-7-02 and the high-resolution data, the method of the present invention is the only method that examines the statistical significance of each biomarker. This ensures the statistical validity of the selected biomarker set from the sample to the population. In accordance with the present invention, only biomarkers significantly different between the groups in expression intensities are selected as candidate biomarkers for the ensuing discriminant analysis. Other algorithms, however, often admit biomarkers that are not statistically valid into the final model. For example, the PROTEOME QUEST (genetic algorithm and self-organizing map software for implementing pattern discovery) algorithm almost invariably admits invalid biomarkers into the final model. The percentage of invalid markers admitted by such algorithms has ranged from 43% to 100%.

One way to establish the significance of the biomarkers identified by the exemplary method of the present invention is to identify and study the cell and molecular biology in terms of physiologic function and/or diagnostic penetrance. Alternatively, the significance, or lack of significance for any biomarker subsets will also become apparent when the number of samples increases 10-100 fold.

Another way to validate the subset of predictive biomarkers is to compare the proteomic analysis with that of an established predictor of disease. For example, in the case of prostate cancer, as a single biomarker, prostate specific antigen (PSA), either total or complex, possesses a marked specificity and diagnostic efficacy of 90-92%, but a low sensitivity of 54-56%. This is primarily due to elevated levels of PSA in benign prostate hyperplasia. Nevertheless, comparing clinically diagnosed prostate cancer patients that are also PSA positive with a serum protein profile analysis in accordance with the present invention should provide a specific subset of proteomic markers that are positively correlated with PSA. These data can then be stratified based upon different PSA levels and in concert with both PSA and potentially other suggested biomarkers such as hyaluronidase, alpha-methyl-CoA racemase and the mucin-like epithelial polypeptide Ca15-3.

An outcome from the application of the present invention to such analysis will be to provide specific phenotype information for a given subset of cancer types. This could be accomplished if sufficient tissue samples remain available to expand the molecular phenotyping of a particular tumor. In the case of breast cancer, in addition to estrogen receptor, progesterone receptor and Ki67, this might include analysis of BRCA1, BRCA2, HER2 and ErkU2.

As the biological signals become more specific, the overall biomarker pattern may become weaker (due to a decrease in the number of valid markers). From a cell biological approach, this will make it possible to better define the biomarkers to be identified. From the mathematical side, however, the detection and discrimination from a complex serum pattern will become more computationally expensive. Algorithms to cluster groups of markers having similar performance will be able to address some of these issues. Exemplary clustering procedures are described more fully below. Furthermore, as the purity of the representative biomarker components improves, the number of non-relevant biomarkers present in the profile will be reduced, thereby increasing the sensitivity and specificity of the statistical analysis.

Multiple Group Classification Analysis and Filtration of Prognostic Factors

As discussed herein, the present inventive system and method is not limited to comparing, classifying or categorizing data into only two groups or categories. The inventive system and method can compare, classify or categorize data into multiple groups or categories. This capability is useful, for example, in classifying subjects into multiple groups in accordance, for example, disease states, treatment responses or stages, and the presence of cofactors or prognostic conditions, among others. For instance, in applying the present invention to the study of diseases such as cancer, it has been observed that the expression levels of certain significant markers are highly variable among subjects with cancer while relatively stable among unaffected subjects. It is possible that these biomarkers are related to specific stages of cancer, differences in individual genetics (e.g. race) or other prognostic factors such as weight, nutritional status or age. Data can be stratified to not only differentiate between two groups (e.g., unaffected and cancer patients), but also the simultaneous classification of subjects within the same disease (e.g., stages of cancer progression and/or tumor subtypes).

In accordance with an embodiment of the present invention, subjects can be classified into multiple groups, for example with multiple disease states, treatment responses or stages, or with different cofactors or prognostic conditions. In such an embodiment, the t/z statistical map for two-group classification, described above, is replaced with a multi-group and repeated measure generalization known as the ANOVA F-map. Markers exceeding the F-map threshold via the random field theory are selected for the multiple group classification. Using random field theory, the critical test value or threshold is determined from the relationship between the experiment-wise error rate a and the critical value f which is given by the following expression:

$$\alpha \approx \int_f^\infty \frac{\Gamma\left(\frac{v+w-2}{2}\right)}{\Gamma\left(\frac{v}{2}\right)\Gamma\left(\frac{w}{2}\right)} \frac{w}{v}\left(\frac{wu}{v}\right)^{\frac{w}{2}-1}\left(1+\frac{wu}{v}\right)^{-\frac{v+w}{2}} du + \frac{2K\sqrt{\ln 2}}{(FWHM)\sqrt{\pi}} \frac{\Gamma\left(\frac{v+w-1}{2}\right)}{\Gamma\left(\frac{v}{2}\right)\Gamma\left(\frac{w}{2}\right)}\left(\frac{wf}{v}\right)^{\frac{w-1}{2}}\left(1-\frac{wf}{v}\right)^{1-\frac{v+w}{2}} \quad \text{(Eq. 9)}$$

K is the total number of markers along the spectrum, and w and v are the degrees of freedom for the ANOVA F-test.

To select markers that are differentially expressed among groups due to the underlying disease and not due to other differences among the groups due to certain prognostic factors such as age, the ANOVA F-map can be replaced with an Analysis of Variance-Covariance (ANOCOVA) F-map whenever necessary. The significant marker threshold can again be determined by Eq. 9.

Thus, by replacing the threshold determined by RFT (as described above) with the F-map threshold, the significant marker selection procedure can be extended from a two-group classification to multiple group classifications and classification incorporating relevant prognostic factors such as medical history or age.

Following this pre-marker selection procedure, there are several classification procedures that can be used, including discriminant analysis classification (i.e. the K-nearest neighbor or the kernel classifier); statistical scoring; or two-level clustering, described below. All three can be extended to multiple group classifications. The extension is straightforward for the discriminant and the cluster analyses.

Extending statistical scoring to multiple group classification involves sequential likelihood ratio tests illustrated as follows. For example, there are three groups and the scores for a given subject place the subject closest to group 2, intermediate with 1, and farthest from 3. The first likelihood ratio test will be between group 2 and 1. If the likelihood ratio is beyond an upper threshold, the subject is classified into group 2 and the test will stop. If the likelihood ratio falls between the upper and lower thresholds, the subject can be either in group 2 or 1. If the likelihood ratio is below the lower threshold and thus the subject is classified into group 1, a further test will commence between 1 and 3 to determine whether the subject can be clearly classified into group 1 or whether the subject could belong to either group 1 or 3.

Another related consideration is the analysis of data obtained from repeated measurements. Repeated measurements of the same subject are useful, for example, to follow disease progression and treatment effects in the same patient; assess the information content arising from different hardware or specimen preparation procedures; or to establish consistency of measurement. The outcome of a repeated measures analysis will be a set of markers and a training set sufficient to determine whether a subject changes categories (e.g. cancerous or non-cancerous) within the sequence of repeated measures. In accordance with an exemplary embodiment, repeated measures ANOVA is performed at each marker to examine whether the expression intensities are equal from spectrum to spectrum or from time to time. Multiple-test correction for the repeated measures ANOVA F-tests are again performed and significant thresholds determined using the above described procedure based on random field theory.

Marker Correlation Analysis

In an aspect of the present invention, a marker correlation analysis tool is provided for algorithm comparison and marker set comparison. A robust outlier detection mechanism is also provided.

A marker correlation analysis procedure in accordance with the present invention comprises two stages. In a first stage, a k-means classifier is adopted to cluster subjects with highly similar mass spectrum profiles. These clusters are subsequently classified in a hierarchical tree structure, formed by weakening the notions of similarity, so that larger groups are classified as similar as one progresses along the tree hierarchy. In a second stage, the branches and nodes of the classification tree are subsequently examined for outliers.

The same two-stage clustering algorithm for outlier detection also serves naturally as a clustering engine. As an example of comparison of algorithms, various spectrum normalization methods using mean, median, or maxima, on a global or regional scale may be used. A set of robust markers that are significant under different normalization methods will be identified and their classification performance examined. The marker correlation analysis tool based on multiple and canonical correlation is an extension of the marker clustering analysis. Marker clustering bins highly correlated individual markers together while the marker correlation tools ascertain the relationship of an individual marker to a set of markers or the relationship between two sets of markers. This is helpful in selecting competing high performance marker sets. A high correlation between marker sets indicates that both have the same information content and thus either one can be adopted. A low correlation indicates complimentary/independent information content and thus both sets should be examined for a complete profiling. An additional application of the marker correlation tool is to examine the relationships between existing markers (e.g. PSA) and newly identified markers (e.g., mass spectrometric biomarkers).

Discriminant analysis and clustering analysis are two types of classification methods. The discriminant analysis procedure (e.g. the l-nearest or the kernel method) described above, classifies subjects into predefined groups. It does not seek other natural clusters that may be embedded in the data. It will not be able to identify outliers due to sample contamination, instrument misalignment or human error (for example, a male sample was wrongly labeled as that from a female). Clustering analysis, however, does not require predefined categories and instead seeks the natural clusters embedded within the data. This also offers a natural solution for outlier detection because an outlier tends to be in a cluster of its own. Furthermore, clusters of outliers are usually located farther apart from the other clusters in a classification tree.

In an aspect of the present invention, a two-level clustering engine is provided. The first level is a k-mean clustering algorithm using the l-correlation dissimilarity measure. It is a dimension reduction scheme as well as an outlier detection mechanism where spectra with similar shapes will be clustered together. Single-point/spectrum clusters can be examined as potential outliers. The second level clustering is defined by modifying the criteria for similarity. It clusters the first level clusters, each represented by its mean or median, in a hierarchical classification tree. Nodes and branches falling farther apart from the majority can be examined as potential outliers as well.

Outliers can arise for a variety of reasons, including, for example, sample contamination, instrument misalignment, or human error. For quality control purposes, one must detect and delete the outliers prior to the diagnostic stage. In one approach, a sample is classified as an outlier if its coefficient of variation exceeds certain boundary values at at least one m/z value. Such m/z values, however, are often not included in the final classification model. This in turn, would cause overly large false rejection rates.

The exemplary two-level clustering algorithm of the present invention is more robust in the detection of outliers because only the significant markers, that are a very small subset of the entire spectrum, will be used towards the classification. Thus, with the two-level clustering algorithm, a sample is declared an outlier only if it exceeds a certain boundary for any of the significant markers.

In a further aspect of the present invention, the correlation between marker sets is analyzed to determine whether two or more marker sets contain the same or complementary information. A related issue is gauging the relationship between existing markers (e.g. PSA or CA125) and new proteomics marker sets. Another area of interest is to correlate the genetics, clinical or other prognostic factors with the proteomics markers.

In an exemplary embodiment, canonical correlation is performed to evaluate linear the relationships between selected marker sets. Principal component analysis is preferably performed for dimensional reduction prior to the correlation analysis.

Canonical correlation is essentially the Pearson correlation between the linear combination of variables in one set and the linear combination of variables from another set. The pair of linear combinations having the largest correlation is determined first. Next, the pair of linear combinations having the largest correlation among all pairs uncorrelated with the initially selected pair is identified, and so on. The pairs of linear combinations are called the canonical variables, and their correlations are called the canonical correlations. The first canonical correlation, which is often the only significant one in most circumstances, is usually adopted to describe the inter-class correlation. Its significance is determined by a statistic termed Wilks' Lambda.

Small sample size and large dimensionality as is common in proteomics studies would frequently render the degrees of freedom insufficient to detect any significant canonical correlation. For each class, major principal components (PCs) accounting for most of the variations will be selected. Furthermore, Pearson correlations of the selected PCs will be obtained and PCs from one marker set that are not significantly correlated with PCs from the other set will be dropped. Canonical correlations will then be obtained using the remaining PCs.

It is very likely that the relationship between two marker sets is not linear. In an exemplary embodiment, extensions to nonlinear canonical correlations in the polynomial space are used. In addition, the canonical correlations can be extended to account for prognostic factors such as age or race by replacing each marker intensity value by its residual from a regression with the prognostic factors as independent variables. The resulting canonical correlations on the residuals will be free of the influence of these prognostic factors.

The marker correlation tool of the present invention can be used to gauge relationship/information overlap between any two sets of variables including genetic markers, proteomics markers, other clinical variables, and prognostic factors such as age.

Improving Efficiency, Specificity and Sensitivity

With the rapid increase in instrumental accuracy, the number of m/z values along a single proteomic mass spectrum has increased from ~15,000 (low-resolution) to ~300,000 (QSTAR) and likely to ~3,000,000 (higher-resolution QSTAR). This has created serious computational difficulties for all diagnostic algorithms. One approach has been to bin adjacent markers (e.g., 50) to reduce the QSTAR data by 50 fold to that of a low-resolution equivalent. By doing so, however, the richer information provided by higher resolution instrumentation is not effectively utilized. To improve the statistical power and the computational efficiency of the statistical detection algorithm, the present invention provides, in an exemplary embodiment, a combination of marker clustering and parallel feature selection algorithms. Marker clustering is based on the K-mean algorithm, which, starting from a single marker, sequentially groups each new marker as being near, and thus added to, some already defined cluster or, if no nearby cluster exists, as starting a new cluster. The algorithm depends on the notion of distance, which is 1−r, where r is the Pearson correlation between two markers across the subjects. After grouping markers into clusters which show similar discriminating behavior, redundancy is avoided by selecting a representative marker from each group. The number of groups is significantly smaller than the number of valid markers, so that the combinatorial complexity of the best subset selection is reduced.

Due to the high dimensionality of the data, it is computationally intensive to process the entire data at one time matching data points on multiple features. The features generally express the result of an approximate, suboptimal best subset selection process. Instead, by implementing several classifiers in parallel, each focusing on the identification of a single feature, for example markers lying within a restricted window of the full spectrum, the classification by multiple features can be accomplished more swiftly. The parallel feature selection algorithm can be readily applied for marker selection. Optimal marker sets are derived from each marker subset/spectrum sub-interval. These optimal marker sets are subsequently merged and further selected via the best-subset or stepwise marker selection algorithms.

Applications of the Present Invention

The present invention is not limited to the analysis of biological and chemical data. A wide variety of data sets from various fields can be analyzed, including any complex data set that can be fit to a Gaussian, Lorenzian, or similar distribution can be analyzed using this invention.

The comprehensive statistical method of the present invention can be applied to analyze any type of raw data, including clinical or environmental data where the sample may be, e.g., water, air, soil, serum, blood, saliva, plasma, nipple aspirate, synovial fluid, cerebrospinal fluid, sweat, urine, fecal matter, tears, bronchial lavage, swabbings, needle aspirant, semen, vaginal fluid, pre-ejaculate, etc., to carry out, e.g., screening for contaminants, pathologic diagnosis, toxicity status, efficacy of a drug, screening or prognosis of a disease. In fact, the processor 100 of the present invention can analyze any data that can be expressed with common coordinates. That is, the multiple sets of data can be mapped into the same coordinate system, thereby enabling comparison between multiple sets of data. The processor 100 of the present invention can analyze data from mass spectroscopy, liquid chromatography, two-dimensional gel chromatography, gas chromatography, etc.

A listing of various applications and any relevant considerations will now be discussed. As can be understood, the applicability of the present invention is not limited to the listed applications and this list is meant to be illustrative only.

Financial/Commercial/Economic

In an exemplary embodiment, the present invention can be used to analyze the trading of securities. For example, when a stock is trading in an aberrant manner due to insider information, the price of the stock may fluctuate in a detectable manner. The present invention can identify such stocks based on their trading patterns and can be used to investigate suspicious activities or to allow investors to better understand the market behavior of such stocks.

In another exemplary embodiment, the present invention can be used for market analysis to better understand the behavior of consumers and their spending patterns.

Environmental/Geological, Sociological

In an exemplary embodiment, the present invention can be used to analyze environmental data, such as for detecting environmental contaminants, using a variety of sample types (e.g., air, water, soil). The present invention can be used also analyze, geological data including, for example, seismic data and radio mapping data.

Disease Diagnosis, Prognosis, Management

The present invention has multiple utilities including, but not limited to, utilities that require the comparison of one or more proteins, either known or unknown, between samples or between a sample and a standard. In general, the methods and apparatus of the present invention have utility in proteome research. In an exemplary embodiment, the present invention is used for the diagnosis, prognosis and management of a disease or condition. The key to the development of assays for diagnostic or prognostic assays is the ability to detect a few marker molecules, often proteins, that are differentially expressed in affected patients. Since the variety and amounts of molecules circulating in the blood or in other biological samples (e.g., cerebrospinal fluid, cell culture, urine, sweat, buccal swab, tissue biopsy, or aspiration sample) at any given moment may differ substantially from one individual to another, the methods and systems described herein can be used to recognize patterns of the disease state or related pattern and thereby provide information as to the disease or condition diagnosis, prognosis, or manamgement.

The present invention is useful for detecting and following the course of any cancer or any disease that like cancer results from acquire genetic mutations or any condition which leads to the production of an abnormal product that may be dectable in blood, urine, etc. or any other type of sample.

In addition to the aforementioned, the present invention is applicable to any disease or disease state that can be classified in accordance with quantitavily expressable characteristics including, for example, cardiopulmonary diseases, autoimmune diseases, Alzheimer's disease, arthritis, infectious diseases, and allergies.

Cancer has become one of the leading causes of death in the Western world, second only to heart disease. Current estimates project that one person in three in the U.S. will develop cancer, and that one person in five will die from cancer. Cancers can be viewed as altered cells that have lost the normal growth-regulating mechanisms.

The present invention can be used for the prognosis, diagnosis, and management of cancer. Particular cancers for which diagnosis or prognosis using the method of the current invention include, for example carcinomas, melanomas, lymphomas, sarcomas, blastomas, leukemias, myelomas, and neural tumors. Particular cancer states contemplated by the present invention include melanoma, non-small cell lung, small-cell lung, lung, hepatocarcinoma, retinoblastoma, astrocytoma, glioblastoma, leukemia, neuroblastoma, head, neck, breast, pancreatic, prostate, renal, bone, testicular, ovarian, mesothelioma, cervical, gastrointestinal, lymphoma, brain, colon, prostate, and bladder. Other diseases that can be diagnosed, managed, or given a prognosis include rheumatoid arthritis, inflammatory bowel disease, osteoarthritis, leiomyomas, ademonas, lipomas, hemangiomas, fibromas, vascular occlusion, restenosis, atherosclerosis, pre-neoplastic lesions, carcinoma in situ, oral hairy leukoplakia and psoriasis.

Other Medical and Biological Applications

The present invention can be applied to a wide variety of other medical uses including, for example, genotyping, isotyping, tissue typing, determining the efficacy of drugs or therapies (alone or in combination), predicting and analyzing drug-drug interactions, determining the state of perturbation of a body organ, and detecting the presence of one or more pathogens.

The present invention is useful for the analysis of gene expression profiles. The data obtained from measuring the transcriptional rate of genes can be analyzed in accordance with the present invention to determine, for example, which genesets are co-regulated as determined from the correlation of gene expression. The transcriptional rate can be measured by techniques of hybridization to arrays of nucleic acid or nucleic acid mimic probes or by other gene expression technologies. However measured, the result is either the absolute, relative amounts of transcripts or response data including values representing RNA abundance ratios, which usually reflect DNA expression ratios (in the absence of differences in RNA degradation rates). In various embodiments of the present invention, aspects of the biological state other than the transcriptional state, such as the translational state, the activity state, or mixed aspects can be measured. Preferably, measurement of the transcriptional state is made by hybridization to transcript arrays.

In a preferred embodiment, the present invention makes use of "transcript arrays" (also called herein "microarrays"). Transcript arrays can be employed for analyzing the transcriptional state in a biological sample and especially for measuring the transcriptional states of a biological sample exposed to graded levels of a drug of interest or to graded perturbations to a biological pathway of interest. In one embodiment, transcript arrays are produced by hybridizing detectably labeled polynucleotides representing the mRNA transcripts present in a cell (e.g., fluorescently labeled cDNA synthesized from total cell mRNA) to a microarray.

Potential drug targets and/or candidates can also be identified using the present invention. For example, the present invention can be utilized to identify proteins that are differentially expressed in diseased cells as compared to normal cells. Such differentially expressed proteins can serve as targets for drugs or serve as a potential therapeutic. In a related fashion, the methods can be used in toxicology studies to identify proteins that are differentially expressed in response to particular toxicants. Such differentially expressed proteins can serve as potential targets or as potential antidotes for particular toxic compounds or challenges. This technique, because of the high discrimination power, can facilitate such investigations because these techniques enable proteins even in low abundance to be detected, which makes it easier to identify real differences in expression between different samples.

The effect of chemical moieties or a combination of moieties on protein expression patterns can be analyzed. Alterations to the chemical moiety or combination can then be made and protein expression reassessed to determine what effect if any the alteration has on protein expression. Such studies can be useful, for example, in making derivatives of a lead compound identified during initial drug screening trials.

Data Sources

The data that can be analyzed in accordance with the present invention may be obtained from any of a number of sources and instruments using various techniques. Such sources and relevant considerations for each will now be discussed.

As already discussed, a source of data for an exemplary embodiment of the present invention includes the mass spectrometer (MS). Mass spectrometry requires that the sample be ionized; it is then passed through a mass discriminator to a mass detector. Two ionization methods are electrospray ionization (ESI) and matrix-assisted laser desorption (MALDI). There are also various mass discriminators that may be used, including, for example, time-of-flight (TOF), a quadrupole ion trap, a double quadrapole, or a triple quadrapole. MS/MS may also be used; where MS involves the collective mass analysis of several peptides (i.e. peptide mass fingerprint), MS/MS analysis is a measurement based on a single peptide and the fragments derived from it via a collisional or decay process. Two basic strategies have been proposed for the MS identification of proteins after separation: mass profile fingerprinting and sequencing of one or more peptide domains by MS/MS. Refinements in both of these techniques have also reduced the amount of individual proteins needed to achieve signature detection. One particularly preferred MS instrument that may be used is the MALDI-TOF/MS. Surface enhanced laser desorption ionization (SELDI) MS which consists of two closely linked techniques, a MALDI-TOF MS coupled with a pre-chromatography step based upon solid phase absorption on a multi-platform chip interface may be used. An instrument for this technique is produced by Ciphergen.

Other spectral analysis techniques may also be used to obtain datasets for analysis by the present invention. These include fluorescence spectroscopy, IR spectroscopy, including FT-IR spectroscopy, laser microscopy including scanning confocal laser microscopy. Raman spectroscopy, including surface enhance Raman (SERS) and resonance Raman, chemiluminescence, electrical phenomenology UV-Vis spectroscopy, including reflection absorption, absorption and transmission, and near-IR spectroscopy.

Nuclear magnetic resonance (NMR), including 2D NMR may be used to provide biological datasets for analysis by the present current invention. MRIs may also be used.

X-Ray diffraction data collected in the time or frequency domain may also be used.

Electrophoresis, such as two-dimensional gel electrophoresis is often used to separate components in the biological sample before it is detected by the MS or other measurement instrument. The electrophoratic system used may be either one or two dimensional.

Capillary electrophoresis (CE) is a different type of electrophoresis, and involves resolving components in a mixture within a capillary to which an electric field is applied.

Isoelectric focusing is an electrophoretic method in which zwitterionic substances such as proteins are separated on the basis of their isoelectric points (PI).

Capillary isoelectric focusing (CIEF) involves separating analytes such as proteins within a pH gradient according to their isoelectric point (i.e., the pH at which the analyte has no net charge) of the analytes. A second method, capillary zone electrophoresis (CZE) fractionates analytes on the basis of their intrinsic charge-to-mass ratio. Capillary gel electrophoresis (CGE) is designed to separate proteins according to their molecular weight.

Capillary zone electrophoresis is an electrophoretic method conducted in free solution without a gel matrix and results in the separation of molecules such as proteins based upon their intrinsic charge-to-mass ratio.

Any type of technique capable of separating proteins can be utilized. Suitable methods include, but are not limited to, HPLC, ion exchange chromatography and affinity chromatography. HPLC, GC, or other separation techniques.

Samples may be introduced into the spectrometers or other devices to obtain the raw data for analysis. Alternatively, samples may come from a device that separates, processes, or otherwise alters the sample before detection. These devices include but are not limited to biochips, lab-on-a-chip, microchip, DNA-based microarrays, other array devices, and microfluidicsystems.

Biological data can be from health data, clinical data, or from a biological sample, (e.g., a biological sample from a human, e.g., serum, blood, saliva, plasma, nipple aspirants, synovial fluids, cerebrospinal fluids, sweat, urine, fecal matter, tears, bronchial lavage, swabbings, needle aspirantas, semen, vaginal fluids, pre-ejaculate, etc.), etc. which is analyzed to determine the biological state of the donor. The biological state can be a pathologic diagnosis, toxicity state, efficacy of a drug, prognosis of a disease, etc. The biological sample may be, for example, blood, cerebrospinal fluid, cell culture, urine, sweat, buccal swab, tissue biopsy, or aspiration sample.

For any given clinical symptom, there can be one, two, dozens, or possibly hundreds of causative agents or targets for the probes of the diagnostic device. A target can be one or more microbes such bacteria, viruses, mycoplasma, rickettsia, chlamydia, protozoa, plant cells (such as algae and pollens), or fimgi. A target can also be a genetic disorder such as a single nucleotide polymorphism (SNP), a specific gene that is not normally present or expressed, or not present in multiple copies, or a mutation in a normally present gene. A target can also be a therapeutic optimization factor. For example, a target can be a specific microbial gene that renders a particular microbe susceptible or resistant to a particular drug. A target can also be a particular genetic sequence in a subject that makes the subject resistant, tolerant, or intolerant (allergic) to a particular drug. These types of targets can be used to develop a specific, tailored, and optimized therapeutic regimen. In addition, the targets can be selected to provide results that are most accepted by physicians and/or clinicians.

One goal of target selection is to select a number of targets (i.e., associated with possible causes of a specific symptom) that provides a high level of reliability that one of the selected targets is the cause of the symptom, and optionally to select additional targets that can be used to optimize therapy. In other words, the goal is to select targets that are the most likely to be the cause of the symptom. For example, if there are 50 possible targets that can cause a symptom, but only 10 targets are known to cause 90% of the clinically observed instances of a given symptom, then a diagnostic device might include probes (e.g., 10 or more probes) to detect only those 10 targets to provide a sufficient level of reliability. This device would not provide a positive result if the cause of the symptom in a subject happens to be one of the targets in the 10% not detected by the device. A more sophisticated diagnostic device might include an additional set of probes that are specific for 10 more known targets that together with the first 10 targets are known to cause 99% of the clinically observed instances of the symptom. Either device can include probes designed to optimize therapy. Of course, other scenarios are possible.

To provide a high degree of accuracy, several different probes can be used to detect and/or quantitate a single, specific target. For example, one probe can be designed to specifically bind to one epitope of an antibody target, and a second probe can be designed to specifically bind to a second epitope of the same antibody. In another example, one probe can be specific for an enzyme that is produced by a specific microbe, a second probe can be specific for a specific nucleic acid associated with that microbe, and a third probe can be specific for and antibody in a subject's bloodstream after exposure to the microbe. In addition, numerous probes of the same type can be clustered into separate locations or spots on a substrate to ensure that sample is evenly distributed over the entire array and that even low concentrations of target are detected. Two or more probes that recognize different epitopes of an antibody can also be mixed and placed on the same spot.

In each case, the probes are designed to specifically bind to an analyte that is, or is associated with, a target. For example, if the target is an antibody, the antibody is the analyte. If the target is a microbial gene, then a specific nucleic acid sequence can be the analyte. If the target is a genetic disorder in the subject, then the analyte might be a SNP or a specific mutant nucleic acid sequence.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments oA the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for analyzing biological samples for the classification of multiple sets of mass spectrometer data derived from the biological samples, each set of mass spectrometer data comprising a plurality of candidate markers and each candidate marker being described uniquely by one or more coordinates, the method comprising:
   for at least a portion of the biological samples, perform the steps of:
      ionizing the biological sample to produce ions; and
      detecting the ions by use of a mass spectrometer, to produce mass spectrometer data;
   the method further comprising the steps of:
   selecting a training set of mass spectrometer data, the training set of mass spectrometer data comprising a plurality of sets of mass spectrometer data from two or more groups of mass spectrometer data representing known conditions selected from the multiple sets of mass spectrometer data;
   performing a point-wise test on the training set of mass spectrometer data to calculate a plurality of test statistic values for the candidate markers;
   determining a threshold test statistic value using a multiple-test correction method based on the size of the training set of mass spectrometer data and a selected significance level;
   selecting those candidate markers having a test statistic value with an absolute value that exceeds the threshold;
   selecting a subset of markers from the candidate markers using a best k-subset discriminant method to discriminate among the two or more groups; and
   classifying a testing set of mass spectrometer data comprising a plurality of sets of mass spectrometer data into the two or more groups using the subset of markers; and
   outputting a result of the classifying step to a computer readable medium,
   wherein at least one candidate marker has a test statistic value with an absolute value that exceeds the threshold test statistic value.

2. The method of claim 1, wherein classifying includes determining a quantitative difference in the subset of markers between the plurality of sets of mass spectrometer data comprising the testing set of mass spectrometer data.

3. The method of claim 1, comprising standardizing the multiple sets of mass spectrometer data.

4. The method of claim 1, comprising randomly selecting the training set of mass spectrometer data from the multiple sets of mass spectrometer data.

5. The method of claim 1, comprising presmoothing the multiple sets of mass spectrometer data with a Gaussian kernel.

6. The method of claim 1, wherein the multiple sets of mass spectrometer data comprise spectral mass spectrometer data.

7. The method of claim 1, wherein determining a threshold includes performing multiple-test correction of at least one of the multiple sets of mass spectrometer data.

8. The method of claim 7, wherein performing multiple-test correction includes performing at least one of a random field theory, a Gaussian random field, and a t random field multiple-test correction.

9. The method of claim 1, wherein selecting a subset of markers includes eliminating any duplicative markers.

10. The method of claim 1, comprising checking the candidate markers for variance stability.

11. The method of claim 1, comprising checking the subset of markers for variance stability.

12. A method of detecting cancer from mass spectrometer data of biological samples, comprising:
   for at least a portion of the biological samples, perform the steps of:
      ionizing the biological sample to produce ions; and
      detecting the ions by use of a mass spectrometer, to produce mass spectrometer data;
   the method further comprising the steps of:
   normalizing and smoothing the mass spectrometer data, to produce standardized and smoothed data;
   randomly sampling data that has been standardized and smoothed to divide the standardized and smoothed data into a training set of mass spectrometer data and a testing set of mass spectrometer data, each of the training set and the testing set comprising random samples from subjects affected and unaffected by the disease;
   performing a point-wise test on the training set of mass spectrometer data to determine test statistic values indicative of the difference between corresponding mass spectrometer data values of the samples of the affected and the unaffected subjects;
   determining a threshold test statistic value using a multiple-test correction method based on the size of the training set of mass spectrometer data and a selected significance level;
   selecting candidate markers having mass spectrometer data values, the mass spectrometer data values having a test statistic value with an absolute value that exceeds the threshold;
   selecting a subset of markers from the candidate markers using a best k-subset discriminant method to discriminate between the affected and the unaffected samples of the training set; and
   classifying the testing set of mass spectrometer data as representing affected or unaffected samples using the subset of markers; and
   outputting the result of the classifying step to a computer readable medium,
   wherein at least one candidate marker has a test statistic value with an absolute value that exceeds the threshold test statistic value.

13. The method of claim 12, comprising classifying mass spectrometer data of a test-biological sample as being affected or unaffected using the subset of markers.

14. The method of claim 12, wherein the mass spectrometer data of biological samples comprises spectral intensity values in a spectrum for each of the biological samples, the method comprising pre-processing the mass spectrometer data of biological samples to standardize and smooth the spectral intensity values across the spectrum for each of the biological samples.

15. The method of claim 14, wherein pre-processing includes presmoothing the mass spectrometer data with a Gaussian kernel.

16. The method of claim 12, wherein the test statistic value $t(x)$ for the corresponding data values $y_1(x)$ and $y_2(x)$ corresponding to x is:

$$t(x) = \frac{\overline{y_1(x)} - \overline{y_2(x)}}{\sqrt{s_1^2(x)/n_1 + s_2^2(x)/n_2}}$$

where $\overline{y}_1(x)$, $\overline{y}_2(x)$, $s_1^2(x)$, $s_2^2(x)$ are the means and variances, respectively, of the affected and unaffected samples of the training set and $n_1$ and $n_2$ are the numbers of affected and unaffected samples, respectively, in the training set.

17. The method of claim 12, wherein determining a threshold test statistic value includes performing multiple-test correction of the mass spectrometer data of the training set.

18. The method of claim 12, wherein selecting a subset of markers includes eliminating any duplicative markers.

19. The method of claim 12, comprising checking the candidate markers for variance stability.

20. The method of claim 12, comprising checking the subset of markers for variance stability.

21. The method of claim 12, wherein classifying the testing set includes using normal kernel density estimates with unequal bandwidth of the subset of markers.

22. The method of claim 13, wherein classifying mass spectrometer data of the biological sample includes determining a change in a state of the disease using the subset of markers.

23. The method of claim 1, comprising clustering mass spectrometer data.

24. The method of claim 1, comprising clustering markers.

25. The method of claim 1, wherein the multiple sets of biological mass spectrometer data comprise multiple sets of ovarian cancer mass spectrometer data.

26. The method of claim 12, wherein the disease is ovarian cancer.

* * * * *